United States Patent
Harvey et al.

(10) Patent No.: US 10,499,822 B2
(45) Date of Patent: Dec. 10, 2019

(54) METHODS AND SYSTEMS RELATING TO BIOLOGICAL SYSTEMS WITH EMBEDDED MEMS SENSORS

(71) Applicant: The Royal Institution for the Advancement of Learning / McGill University, Montreal (CA)

(72) Inventors: Edward Harvey, Westmount (CA); Vamsy Chodavarapu, St Laurent (CA); Charles Allan, Montreal (CA)

(73) Assignee: The Royal Institution for the Advancement of Learning / McGill University, Montreal (CA)

( * ) Notice: Subject to any disclaimer, the term of this patent is extended or adjusted under 35 U.S.C. 154(b) by 110 days.

(21) Appl. No.: 14/707,329

(22) Filed: May 8, 2015

(65) Prior Publication Data
US 2015/0351648 A1 Dec. 10, 2015

Related U.S. Application Data

(60) Provisional application No. 61/990,757, filed on May 9, 2014.

(51) Int. Cl.
*A61B 5/03* (2006.01)
*A61B 5/07* (2006.01)
*A61B 5/00* (2006.01)

(52) U.S. Cl.
CPC ............. *A61B 5/03* (2013.01); *A61B 5/076* (2013.01); *A61B 5/686* (2013.01); *A61B 2562/028* (2013.01); *A61B 2562/0247* (2013.01)

(58) Field of Classification Search
CPC ...... A61B 5/031; A61B 5/0215; G07C 5/008; G07C 5/0808; B60N 2/0232
See application file for complete search history.

(56) References Cited

U.S. PATENT DOCUMENTS

| | | | |
|---|---|---|---|
| 2003/0220589 A1* | 11/2003 | Leivseth | A61B 5/227 600/591 |
| 2008/0058632 A1* | 3/2008 | Tai | A61B 3/16 600/398 |
| 2009/0216149 A1* | 8/2009 | Neff | A61B 5/031 600/561 |
| 2010/0056985 A1* | 3/2010 | Weber | A61B 1/00082 604/21 |

(Continued)

OTHER PUBLICATIONS

Arbabi S, Brundage SI, Gentilello LM. Near-infrared spectroscopy: a potential method for continuous, transcutaneous monitoring for compartmental syndrome in critically injured patients. J Trauma. Nov. 1999;47(5):829-33.

(Continued)

*Primary Examiner* — Patrick Fernandes
(74) *Attorney, Agent, or Firm* — McDonnell Boehnen Hulbert & Berghoff LLP

(57) ABSTRACT

Small implantable silicon-based devices offer an ability to revolutionize the management of trauma victims. For example, implantable pressure sensors allow the devastating outcomes of compartment syndrome to be minimized through continuous or periodic monitoring whilst being compatible with the ongoing drives to increase out-patient care and reduced hospitalization time. Further, small implantable silicon-based sensor microsystems according to embodiments of the invention whilst being capable of measuring pressures under diverse conditions are easily used by nurses in hospital settings as well as also being easily deployed by paramedical personnel in cases of accidents, natural disasters, war, etc. Beneficially, the implantable sensor microsystem will not interfere with movement of the patient during stabilization, surgery, intensive care stay, outpatient management, etc.

20 Claims, 19 Drawing Sheets

(56) References Cited

U.S. PATENT DOCUMENTS

| | | | |
|---|---|---|---|
| 2011/0160560 A1* | 6/2011 | Stone | A61B 3/16 600/398 |
| 2012/0130219 A1* | 5/2012 | Zhao | A61B 5/0215 600/373 |
| 2012/0238857 A1* | 9/2012 | Wong | A61B 3/16 600/398 |
| 2013/0018413 A1* | 1/2013 | Oral | A61B 17/12186 606/213 |
| 2013/0194540 A1* | 8/2013 | Pugh | A61F 2/1635 351/159.03 |
| 2013/0204202 A1* | 8/2013 | Trombly | A61M 5/16877 604/207 |
| 2013/0289522 A1 | 10/2013 | Musallam et al. | |
| 2013/0292852 A1* | 11/2013 | Fuergut | B81B 7/02 257/777 |

OTHER PUBLICATIONS

Crespo et al., Development of Compartment Syndrome Negatively Impacts Length of Stay and Cost After Tibia Fracture. J. Orthop. Trauma. vol. 29, No. 7, pp. 312-315, Jul. 2015.

Graffte K. Fluoropolymers: Fitting the Bill for Medical Applications, Medical Device and Diagnostic Industry, Oct. 2005, pp. 34-37.

Lee RY, Colville JM, Schuberth JM. Acute Compartment Syndrome of the Leg with Avulsion of the Peroneus Longus Muscle: A Case Report, The Journal of Foot and Ankle Surgery, May-Jun. 2009, pp. 365-367, vol. 48, Issue 3.

Matsen III FA, Windquist RA, Jrugmire JR RB. Diagnosis and management of compartmental syndromes, J. Bone Joint Surg., pp. 286-291, vol. 62, Issue 2, Mar. 1980.

Pearse et al., Acute Compartment Syndrome of the Leg, British Medical Journal, Sep. 14, 2002, pp. 557-558, vol. 325; issue 7364, London.

Sellei et al., Non Invasive Assessment of Acute Compartment Syndrome by Pressure Related Ultrasound: A Cadaver Study, J. Bone Joint Surg., Brit. pp. 521, vol. 94-B, Sep. 14, 2012.

Shadgan, et al. Risk factors for acute compartment syndrome of the leg associated with tibial diaphyseal fractures in adults. J. Orthopaed. Traumatol. vol. 16, pp. 185-192, Dec. 28, 2014.

Keudell et al., Diagnosis and Treatment of acute extremity compartment syndrome. Emergency Surgery 3. Lancet 2015; 386: 1299-1310.

* cited by examiner

METHODS AND SYSTEMS RELATING TO BIOLOGICAL SYSTEMS WITH EMBEDDED MEMS SENSORS

CROSS-REFERENCE TO RELATED APPLICATIONS

This patent application claims the benefit of U.S. Provisional Patent Application U.S. 61/990,757 filed May 9, 2014 entitled "Methods and Systems relating to Biological Systems with Embedded MEMS Sensors", the entire contents of which are included by reference.

FIELD OF THE INVENTION

This invention relates to biomedical sensors and more particularly to implantable silicon-based sensor microsystems exploiting external electromagnetic wave activation.

BACKGROUND OF THE INVENTION

The muscles of the lower limb are bundled into "compartments" surrounded by inelastic connective tissue called fascia. High-energy impact causes swelling and increased pressure within the muscle compartments that reduces blood flow and results in the condition called Acute Compartment Syndrome (ACS), see for example Pearse et al in "Acute Compartment Syndrome of the Leg" (British Medical J., Vol. 325, Iss. 7364, pp. 557-558) and Lee et al in "Acute Compartment Syndrome of the Leg with Avulsion of the Peroneus Longus Muscle: A Case Report" (J. Foot Ankle Surg., Vol. 48, Iss. 3, pp. 365-367), which is a well-recognized and common emergency. This intra-compartmental swelling is the result of increased size of the damaged tissues themselves following acute crush injury or from reperfusion of ischemic areas. It is usually not from a collection of free blood or fluid in the compartments. Presently, there is no reliable and reproducible test that confirms the diagnosis of ACS. A missed diagnosis or failure to cut the fascia to release pressure within a reasonable time, even just a few hours, can result in severe intractable pain, paralysis, and sensory deficits.

Currently, the diagnosis of ACS is made on the basis of physical exam and repeated needle sticks over a short time period to measure intra-compartmental pressures, see for example Falter in "Bedside Procedures in the ICU" (Springer, 2012) and Matsen et al in "Diagnosis and Management of Compartmental Syndromes" (J. Bone Joint Surg., Vol. 62, Iss. 2, pp. 286-291). Missed diagnosis of compartment syndrome continues to be one of most common causes of malpractice lawsuits in USA/Canada. Existing technology for continuous pressure measurements are insensitive, particularly in the deep tissues and compartments, and its use is restricted to highly trained personnel.

The usual cause of this condition is trauma although limb blood vessel surgery, limb blood clots, and hemorrhaging are other causes. However, crush injuries, burns, overly tight bandaging, prolonged compression of a limb during unconsciousness, anticoagulants, hemophilia, and tissue swelling under the skin can increase the risk of ACS. Typical symptoms may include: severe pain; feeling of tightness or fullness of muscles; swollen pale, shiny skin over affected area; and numbness or tingling. Symptoms may develop within 30 minutes to two hours, although in other cases, it may take days.

Undiagnosed compartment syndrome leads to muscle necrosis, contracture, and could eventually result in chronic infection or amputation. The only way to avoid these complications is early recognition and attendant decompression with a fasciotomy (large incision to release the fascial containment of the compartment). A method for the accurate and reproducible diagnosis of ACS, especially in the obtunded, polytrauma or distracted patient is yet to be developed. Resolution or clarification of the diagnosis of ACS would be a great asset for the patient population. Consequently, a large number of trauma surgeons face this diagnostic conundrum on almost a daily basis.

In today's clinical scenario, pressure measurements through the use of repeated needle sticks are the best means of determining the need for a fasciotomy. Although newer technologies, such as ultrasound, see for example Sellei et al in "Non Invasive Assessment of Acute Compartment Syndrome by Pressure Related Ultrasound: A Cadaver Study" (J. Bone Joint Surg., Brit. Vol. 94-B (Supp. XXXVII), pp. 521) and "Shadgan et al in "Diagnostic Techniques in Acute Compartment Syndrome of the Leg" (J. Orthopaedic Trauma, Vol. 22.8, pp. 581-587) and near infrared, see for example Arbabi et al in "Near-Infrared Spectroscopy: A Potential Method for Continuous, Transcutaneous Monitoring for Compartmental Syndrome in Critically Injured Patients" (J. Trauma and Acute Care Surg., Vol. 47, pp. 829), 1999, monitoring are being tested, but they all seem to have major problems with missing compartments and interfering with complete care of the patient.

Accordingly, there is a need for always-on minimally invasive devices that does not interfere with transportation or total care of the patient and allows continuous monitoring over an extended period given symptoms post-incident may take several days. It would be further beneficial to monitor all potential areas of interest without being labor-intensive, relying on highly educated technicians or being excessively user dependent, and offers low cost manufacturing to support widespread. It would be further beneficial for the technology employed to be compatible with integration of other sensor functions allowing in addition to accurately measuring pressure the measurement of oxygen partial pressure and temperature fluctuations in the limb compartments of patients at risk of developing ACS.

It would be further beneficial for temporary in-situ direct pressure monitors to be designed to be compatible with a battery-less Radio Frequency Identification Device (RFID)/Near Field Communication (NFC) platform, allowing the ACS sensors to be powered by wireless transfer of radio frequency electromagnetic energy. These small implantable silicon-based devices will revolutionize the management of trauma victims and minimize the devastating outcomes of compartment syndrome whilst being compatible with the ongoing drives to increased out-patient care and reduced hospitalization time. Whilst the small implantable silicon-based sensor microsystems according to embodiments of the invention are capable of measuring pressures under diverse conditions and being easily used by nurses in hospital settings they can also be easily deployed by paramedical personnel in cases of accidents, natural disasters, war, etc. In some instances the patient may become an outpatient and the monitoring continue until a subsequent outpatient appointment to remove the implanted sensor microsystems occurs. Beneficially, the implantable sensor microsystem will not interfere with movement of the patient during stabilization, surgery, intensive care stay, outpatient management, etc. and will ultimately, transform the management of trauma victims and minimize the devastating outcomes of compartment syndrome.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations in the prior art relating to biomedical sensors and more particularly to implantable silicon-based sensor microsystems exploiting external electromagnetic wave activation.

In accordance with an embodiment of the invention there is provided a device comprising:
an antenna operable over a predetermined wireless frequency range;
a silicon microelectromechanical system (MEMS) circuit comprising at least a pressure sensor incorporating at least one pressure sensing element of a plurality of pressure sensing elements and at least one referenced pressure element of a plurality of reference pressure elements;
a sensor interface circuit for converting the output of the pressure sensor to digital data;
a wireless interface circuit connected to the antenna and the sensor interface circuit, the wireless interface circuit for in a first mode receiving a wireless signal coupled to the antenna to power at least the wireless interface circuit and in a second mode generating a wireless signal to be coupled to the antenna in dependence upon at least the digital data.

In accordance with an embodiment of the invention there is provided a system comprising:
an antenna operable over a predetermined wireless frequency range;
a silicon microelectromechanical system (MEMS) circuit comprising at least a pressure sensor incorporating at least one pressure sensing element of a plurality of pressure sensing elements and at least one referenced pressure element of a plurality of reference pressure elements;
a sensor interface circuit for converting the output of the pressure sensor to digital data;
a wireless interface circuit connected to the antenna and the sensor interface circuit, the wireless interface circuit for in a first mode receiving a wireless signal coupled to the antenna to power at least the wireless interface circuit and in a second mode generating a wireless signal to be coupled to the antenna in dependence upon at least the digital data.

In accordance with an embodiment of the invention there is provided a device comprising:
a silicon microelectromechanical system (MEMS) circuit comprising at least a pressure sensor incorporating at least one pressure sensing element of a plurality of pressure sensing elements and at least one referenced pressure element of a plurality of reference pressure elements; and
a sensor interface circuit for converting the output of the pressure sensor to digital data.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
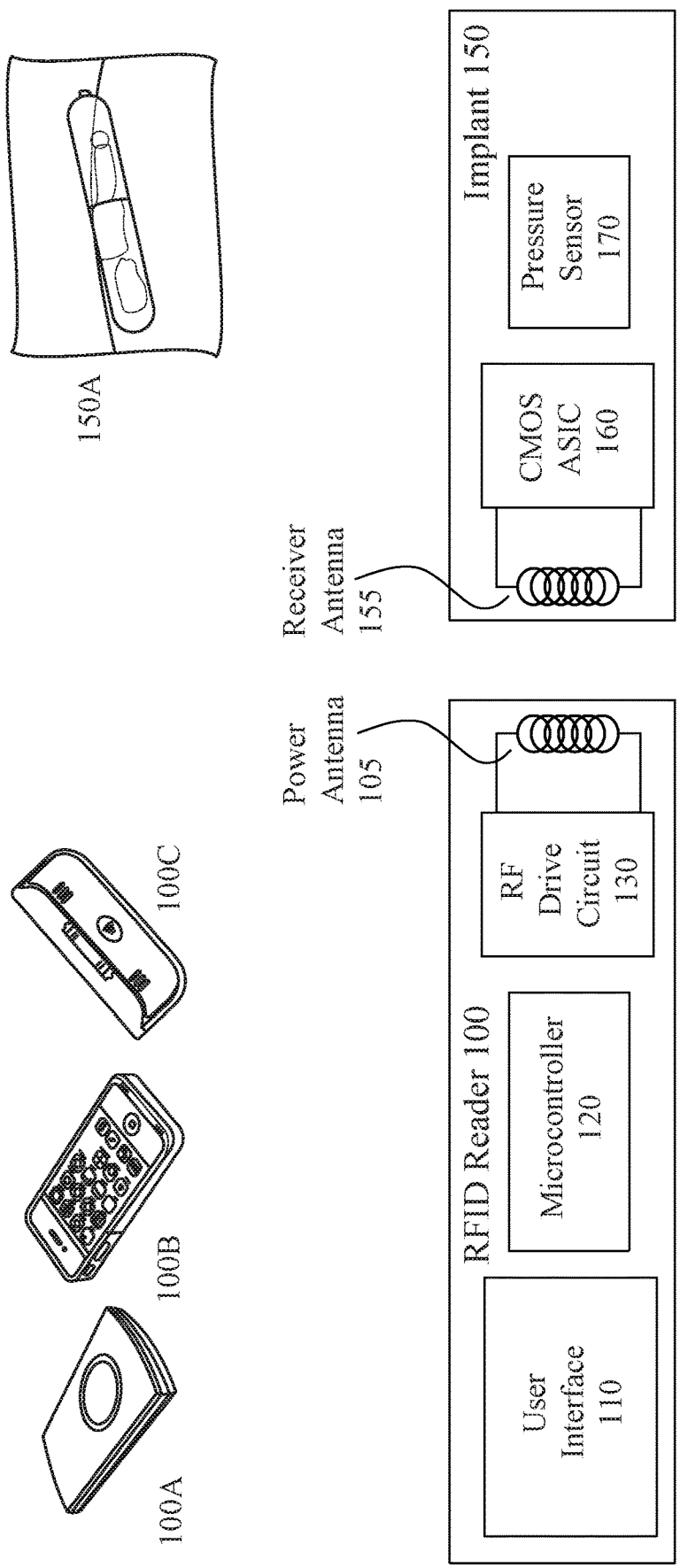
FIG. 1 depicts an implantable sensor with wireless read/power according to an embodiment of the invention.

The present invention is directed to biomedical sensors and more particularly to implantable silicon-based sensor microsystems exploiting external electromagnetic wave activation.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A "portable electronic device" (PED) as used herein and throughout this disclosure, refers to a wireless device used for communications and other applications that requires a battery or other independent form of energy for power. This includes devices, but is not limited to, such as a cellular telephone, smartphone, personal digital assistant (PDA), portable computer, pager, portable multimedia player, portable gaming console, laptop computer, tablet computer, portable medical equipment and an electronic reader.

A "fixed electronic device" (FED) as used herein and throughout this disclosure, refers to a wireless and/or wired device used for communications and other applications that requires connection to a fixed interface to obtain power. This includes, but is not limited to, a laptop computer, a personal computer, a computer server, a kiosk, electronics equipment, medical equipment, a gaming console, a digital set-top box, an analog set-top box, an Internet enabled appliance, an Internet enabled television, and a multimedia player.

"Near field communication" (NFC) as used herein and throughout this disclosure, refers to a set of standards for devices, including PEDs, FEDs, implants, smart labels, smart tags, wearable devices, etc. to establish radio communication with each other by touching them together or bringing them into proximity over a short range. NFC allows contactless transactions, data exchange, and simplified setup of more complex communications such as Wi-Fi. Communication is also possible between an NFC device and an unpowered NFC chip, typically called a "smart tag" or "tag". NFC standards are typically based upon Radio-Frequency IDentification (RFID) standards including, but not limited to, ISO/IEC 14443, FeliCa (Sony's Felicity Card), ISO/IEC 18092, and those defined by the NFC Forum.

"Radio Frequency Identification" (RFID) as used herein and throughout this disclosure, refers to the wireless non-contact use of radio-frequency electromagnetic fields to transfer data, for the purposes of automatically identifying and tracking tags attached to objects and electronically store information. Some tags are powered by and read at short ranges (a few meters) via magnetic fields (electromagnetic induction). Others use a local power source such as a battery, or else have no battery but collect energy from the interrogating EM field, and then act as a passive transponder to emit microwaves or UHF radio waves (i.e., electromagnetic radiation at high frequencies). Battery powered tags may operate at hundreds of meters.

"Wireless" (also known as wireless communications) as used herein and throughout this disclosure, refers to wireless technology, such as radio, to provide and support communications including, but not limited to, point-to-point communication, point-to-multipoint communication, broadcasting, cellular networks and other wireless networks. Such communications may be according to one or more wireless communications standards such as, for example, IEEE 802.11, IEEE 802.15, IEEE 802.16, IEEE 802.20, UMTS, GSM 850, GSM 900, GSM 1800, GSM 1900, GPRS, ITU-R 5.138, ITU-R 5.150, ITU-R 5.280, and IMT-1000.

1. Device Concept and Sensor Capabilities

Over the past several years, tremendous advances in silicon microfabrication techniques have led to the development of miniaturized sensors including pressure, temperature, acceleration, flow, angular acceleration, touch amongst others that have found many applications in video gaming devices, automotive and aerospace industry, process control and industrial monitoring, and medical monitoring. In many instances these exploit MicroElectroMechanical Systems (MEMS). Examples of such MEMS sensors can be found in a variety of prior art publications including Gad-el-Hak in "MEMS: Introduction and Fundamentals" (CRC Press, 2010), Hsu "MEMS & Microsystems: Design, Manufacture, and Nanoscale Engineering" (John Wiley & Sons, 2008), and Korvink et al in "MEMS: A Practical Guide of Design, Analysis, and Applications" (Springer, 2010). Within the descriptions below with respect to embodiments of the invention the inventors describe micromachined ultra-thin membrane based capacitive transducers that are fabricated on a silicon substrate whilst temperatures sensors are typically implemented on-chip with microelectronic signal processing circuitry. However, it would be evident that other pressure sensor designs may be employed as may on-chip temperature sensors, oxygen sensors, chemical sensors, accelerometers, etc. dependent upon the use of battery or battery-less design methodologies for the implanted sensor.

Within the descriptions below the development of pressure, oxygen, temperature sensors, etc. is geared to a single implantable microdevice designed to be powered by wireless transfer of energy through RF spectrum at 13.56 MHz. A commercially available, external radio-frequency reader is passed over the sensor to power the sensor system and to receive discreet data points or the reader can be left near the patient with the implanted sensor for continuous monitoring.

Figure 3B:
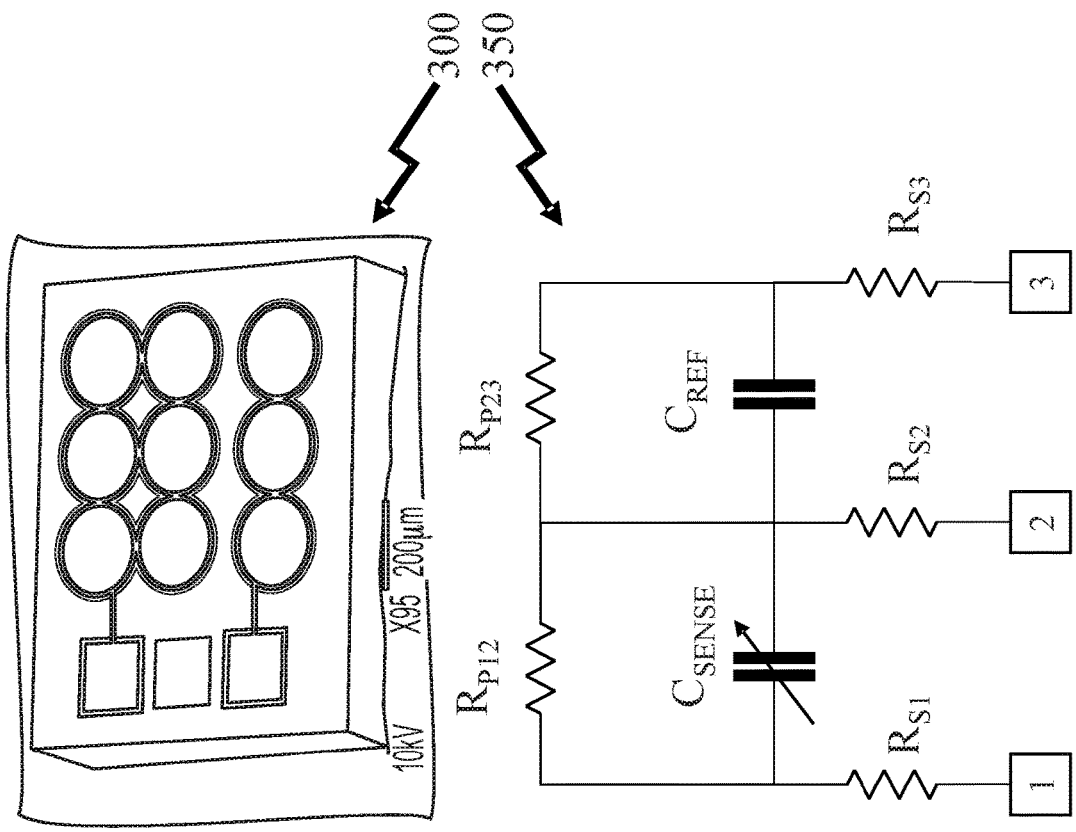
FIG. 3B depicts a MEMS pressure sensor and its equivalent electrical model according to an embodiment of the invention.
Figure 3A:
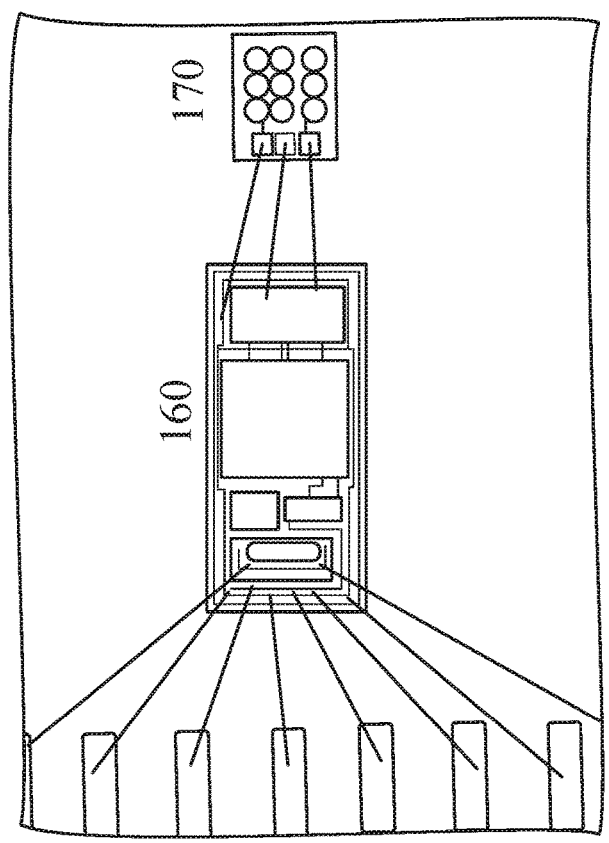
FIG. 3A depicts a microphotograph of a pressure sensor microsystem according to an embodiment of the invention.

1.1 System Overview: Referring to FIG. 1 there is depicted a simplified operational architecture of the sensor system comprising RFID Reader 100 and Implant 150. The Implant 150 typically consists of three components, an implant coil (receiver antenna) 155 for receipt of RF energy and transfer of sensor signals, a Complimentary Metal-Oxide Semiconductor (CMOS) Application Specific Integrated Circuit (ASIC) 160 to condition and regulate the received energy to power the signal processing circuitry and external pressure sensor, and capacitive pressure microsensor 170. Experimental prototypes of the ASIC were implemented using the TSMC 0.18 µm process available from Canada Microelectronics Corporation and is shown in FIG. 3A. Using this CMOS technology a temperature sensor on-chip within the ASIC may be implemented, for example, using a standard silicon bipolar junction transistor (BJT) operating in a diode configuration. As assembled Implant 150 being depicted in image 150A.

Figure 2A:
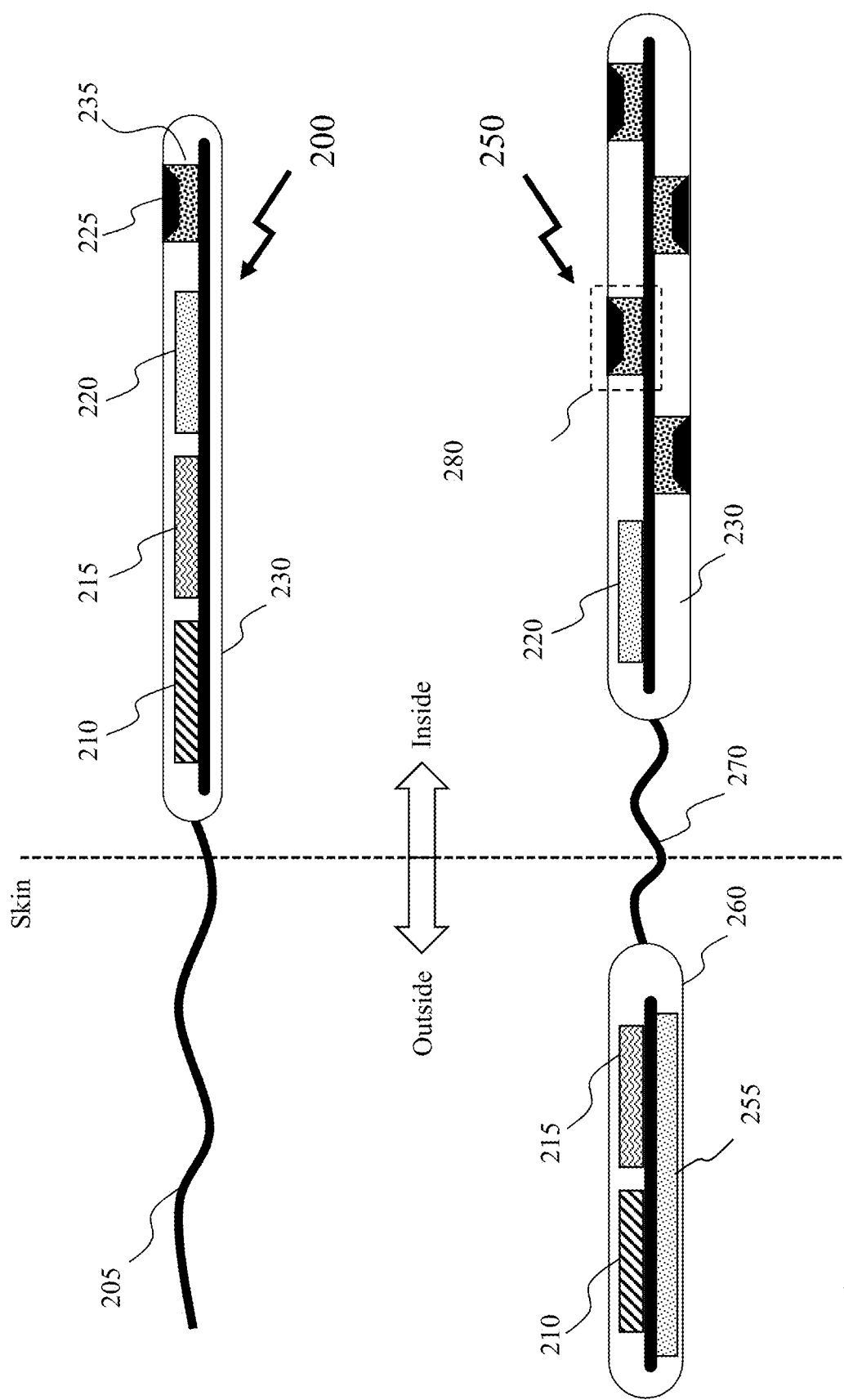
FIG. 2A depicts implantable sensors with implanted and external wireless read/power elements according to embodiments of the invention.

The RFID Reader 100 comprises a reader coil (power antenna) 105, an RF drive circuit 130, a microcontroller 120, and a user interface 110. RFID Reader 100 may, for example, be a handheld dedicated RFID Reader 100A, smartphone 100B, or adapter 100C which provides NFC and RFID Reader/Writer extension capabilities to non-NFC enabled cellular phones. that provides NFC two way communications, RFID read/write and contactless payment capability 1.2 Exemplary System Designs: Referring to FIG. 2A there are depicted first and second embodiments 200 and 250 of the invention in RF and battery powered configurations respectively. First embodiment 200 depicts a system design for RF powered configuration comprising RF antenna 210 which is coupled to RF Integrated Circuit (RFIC) 215 to receive the RF signal to power the implanted sensor and transmit the pressure measurement back to the external reader. Also interfaced to the RFIC 215 is capacitance to digital converter 220 which converts the capacitance of the MEMS pressure sensor 235 to a digital word for transmission to the external reader. The MEMS pressure sensor 235 has a layer of silicone gel 225 disposed above it to couple the MEMS pressure sensor 235 to the PEEK thermoplastic body 230 of the implanted sensor. Also attached to the implanted sensor is a PEEK thermoplastic sleeve (not shown for clarity) fitting over the PEEK thermoplastic body 230 that extends as a tail to the implant sensor such that the tail extends to the outside of the patient's body.

In second embodiment 250 depicts a system design for a battery powered configuration comprising RF antenna 210 which is coupled to RF Integrated Circuit (RFIC) 215 to transmit the pressure measurement back to the external reader. The RFIC 215 being powered by battery 255 which may, in some embodiments of the invention, be charged through RF induction prior to imbedding into the patient and topped up with each reading. The RFIC 215, RF antenna 210 and battery 255 are housed in an outer shell 260 which is coupled to the implanted sensor via a PEEK thermoplastic tail 270 carrying power and data lines to the implanted sensor. The implanted sensor comprises a PEEK thermoplastic body 230 over which a PEEK thermoplastic sleeve (not shown for clarity) fits.

The data and power lines are coupled to capacitance to digital converter 220 which converts the capacitance of the MEMS pressure sensors 235 to a digital word and provides it to the RFIC 215. Each MEMS pressure sensor 235 of the multiple MEMS pressure sensors 235 has a layer of silicone gel 225 disposed above it to couple the MEMS pressure sensor 235 to the PEEK thermoplastic body 230 of the implanted sensor and therein detect the pressure locally within the patient.

In each of the first and second embodiments 200 and 250 the PEEK thermoplastic body 230 may incorporate openings aligning with the MEMS pressure sensors 235 such that these are only separated from the patient's tissue by the PEEK thermoplastic sleeve. Optionally, the PEEK thermoplastic body 230 may be thinned in regions aligning with the MEMS pressure sensors 235.

Figure 2B:
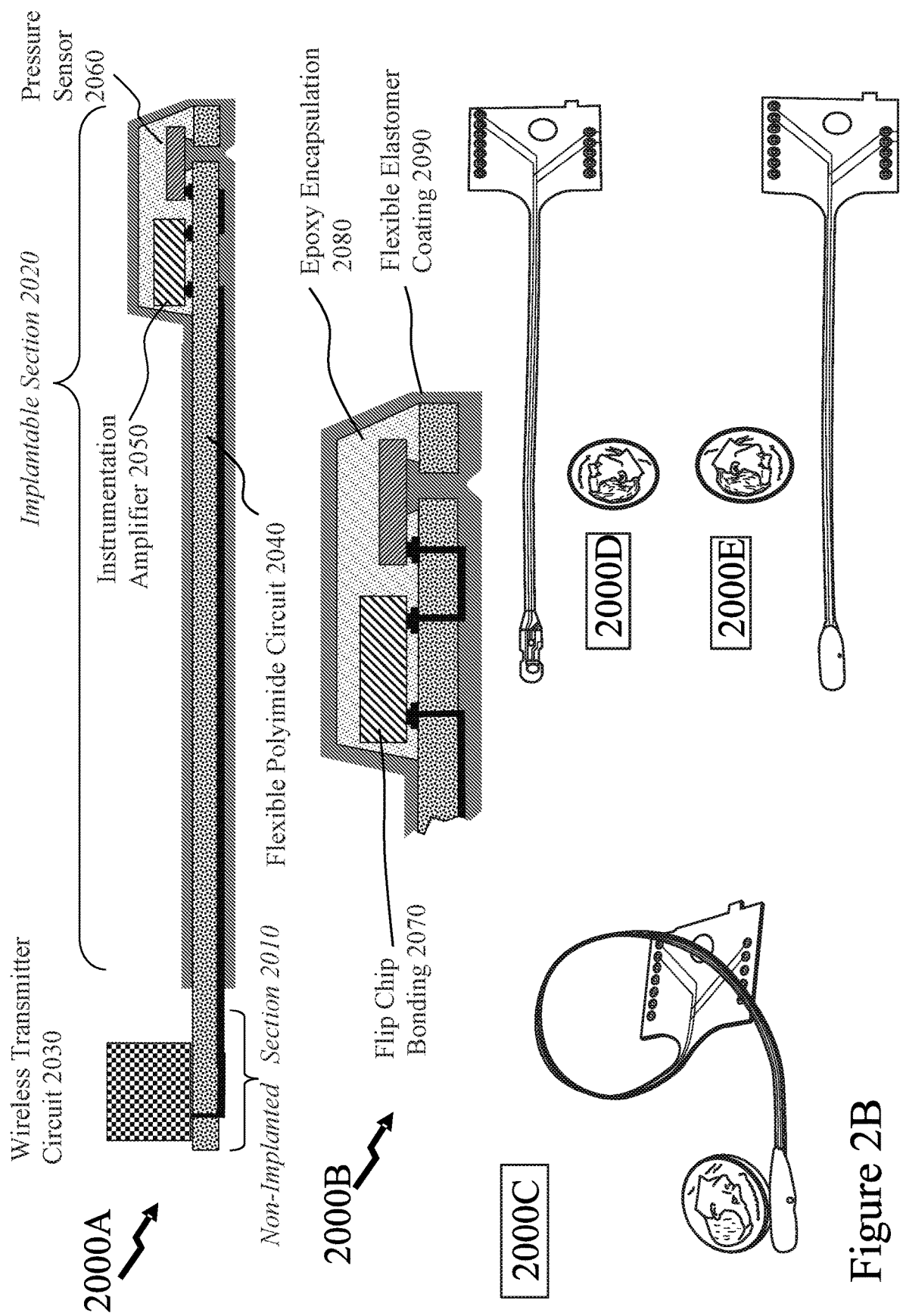
FIG. 2B depicts implantable sensors with external wireless transceiver circuit and electrical connections according to embodiments of the invention.

Now referring to FIG. 2B there are depicted first to fifth images 2000A to 2000E in respect of implantable sensors with external wireless transceiver circuit and electrical connections according to embodiments of the invention. First image 2000A depicts an implantable sensor according to an embodiment of the invention wherein the non-implanted section 2010 supports wireless transmitter circuit 2030, which may for example be a Bluetooth proximity integrated circuit (IC) packaged in a 5 mm×5 mm QFN package or flip-chip bonded bare die with encapsulation. Other short range Bluetooth ICs may be employed as well as others supporting Wireless USB, ANT+, IEEE 802.15.4, 6LowPAN, Zigbee, and Z-Wave. Optionally, the wireless transmitter circuit 2030 may operate on unlicensed ISM channels or be a near-Field Communications (NFC)/Radio Frequency Identity (RFID) based circuit. The wireless transmitter circuit 2030 is electrically connected to the implantable section 2020 and therein an instrumentation amplifier 2050 which is coupled to the pressure sensor 2060. These and the wireless transmitter circuit 2030 are supported upon a flexible polyimide circuit 2040 which is encapsulated within a flexible elastomer coating 2090. The instrumentation amplifier 2050 is mounted via flip-chip bonding 2070 and is encapsulated within an epoxy encapsulant 2080 together with the flip-chip mounted pressure sensor 2060 and then within the flexible elastomer coating 2090. The pressure sensor 2060 is inverted against an opening within the flexible polyimide circuit 2040 such that the external pressure is coupled to the pressure sensor 2060 via the flexible polyimide circuit 2040.

Optionally the epoxy encapsulant 2080 is biocompatible or may be replaced with a biocompatible thermoplastic adhesive or another setting biocompatible encapsulant. The flexible polyimide circuit 2040 may be implemented with gold electrical traces or alternatively aluminum—copper (AlCu). Accordingly, referring to second image 2000B the top region of the implantable section 2020 is depicted showing the flip-chip mounted instrumentation amplifier 2050 and pressure sensor 2060 together with the via within the flexible polyimide circuit 2040.

A test version of the implantable sensor depicted in first and second images 2000A and 2000B is depicted in third to fifth images 2000C to 2000E respectively wherein the non-implanted section 2010 and wireless transmitter circuit 2030 have been replaced by an extended flexible polyimide circuit which terminates in a flexible header compatible with a DIL header socket or equivalent. In third image 2000C the implantable section 2010 is depicted with flexible elastomeric coating 2090 whereas in fourth and fifth images 2000D and 2000E respectively it is shown before and after epoxy encapsulation.

2. Components of the Sensor 2.1 Capacitive Mems Pressure Sensor: A miniature absolute MEMS capacitive pressure sensor is used to measure the pressure. This pressure sensor is designed for various applications such as invasive/noninvasive medical pressure monitoring, industrial, and automotive applications. FIG. 3B depicts the pressure sensor 300 and its electrical model 350, respectively. The dimensions of the pressure sensor may, for example, be typically of dimensions $100 \leq Length \leq 2000$ μm by $100 \leq Width \leq 2000$ μm and $200 \leq Height \leq 1000$ μm where typical bonding pad dimensions are 150 μm×150 μm. The absolute capacitive MEMS pressure sensor consists of several single crystal silicon membranes which are defined by single crystal silicon (Silicon-on-Insulator (SOI) device layer). The dimensions of the pressure sensor die being determined by factors including, but not limited to, diameter of the MEMS sensor element, diameter of the reference MEMS sensor element, the number of MEMS sensor elements, number of reference MEMS sensor elements, bond pad dimensions, electrical interconnect, and the designed operating range of the MEMS pressure sensors which may, for example, be designed over a variety of pressure ranges within part or all of the range from 1 kPA to 250 kPa, for example.

Figure 4A:
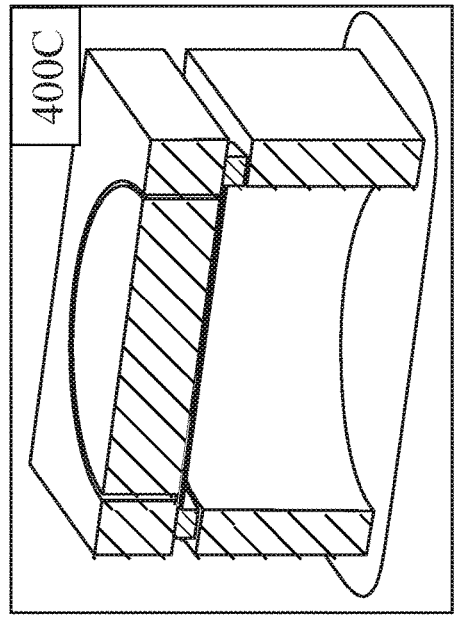
FIG. 4A depicts schematics of an absolute pressure sensor according to an embodiment of the invention.
Figure 4A:
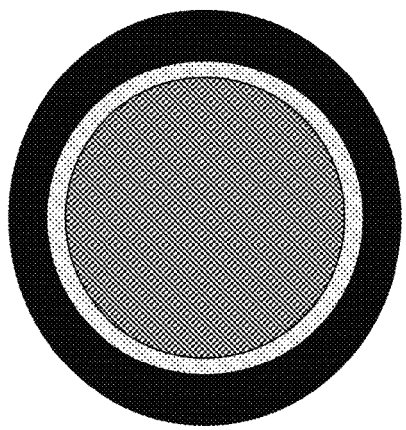
Figure 4A:
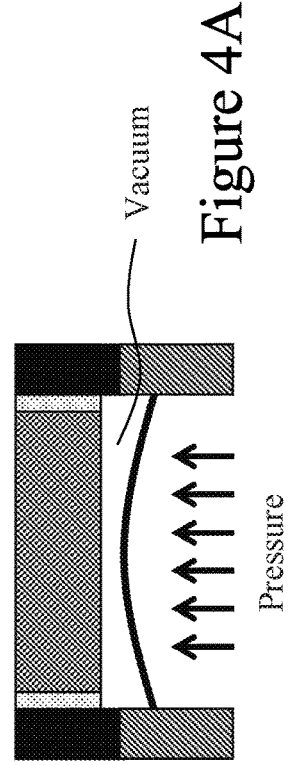
Figure 4A:
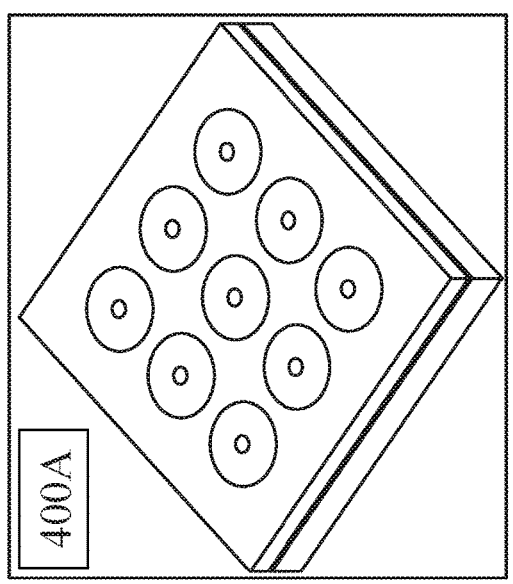
Figure 4A:
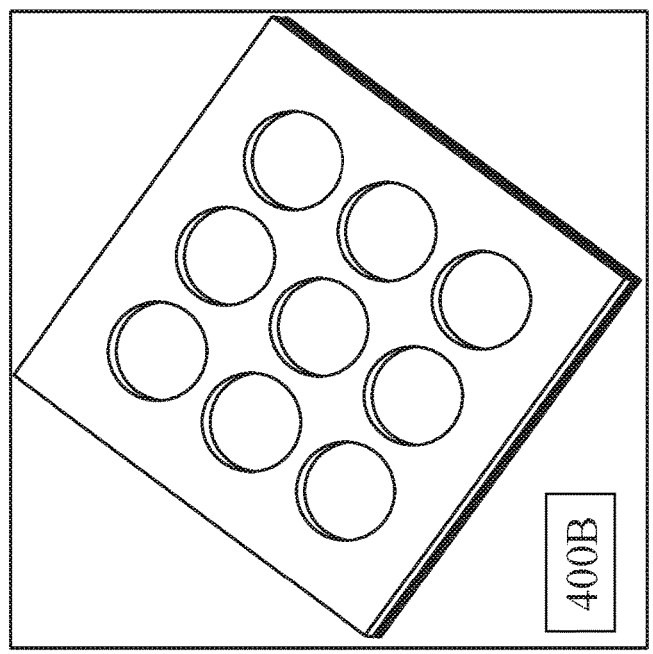

As depicted in FIG. 4A in cross-section 400D and perspective section 400C the absolute pressure sensors are based upon capacitance variations based upon the membrane displacement under pressure where the membrane represents one of the two electrodes constituting the electrical capacitance wherein the electrodes are separated by a thin vacuum region such that the deflection of the membrane is now dependent upon the absolute pressure. Accordingly, the MEMS pressure sensor converts pressure into deflection of the mechanical membrane, converting in turn, this deflection into electrical capacitive change, and then converting the capacitance change into an output voltage signal by means of appropriate readout circuit. As depicted in top side and bottom side perspective views 400A and 400B respectively an exemplary die may include, for example, nine MEMS pressure sensors may be integrated into a single die exploiting a circular membrane undergoing distributed pressure load. As the MEMS manufacturing process allows the cavity pressure between the two electrodes to be close to vacuum, then the sensors allow absolute pressure measurement. Equally, a known pressure may be established within one or more of the MEMS pressure sensors as a pressure reference element. Within the embodiment depicted in FIG. 4A in top side and bottom side perspective views 400A and 400B respectively three sensors may be set to a reference pressure whilst the other 6 are at vacuum as absolute pressure sensors.

Figure 4B:
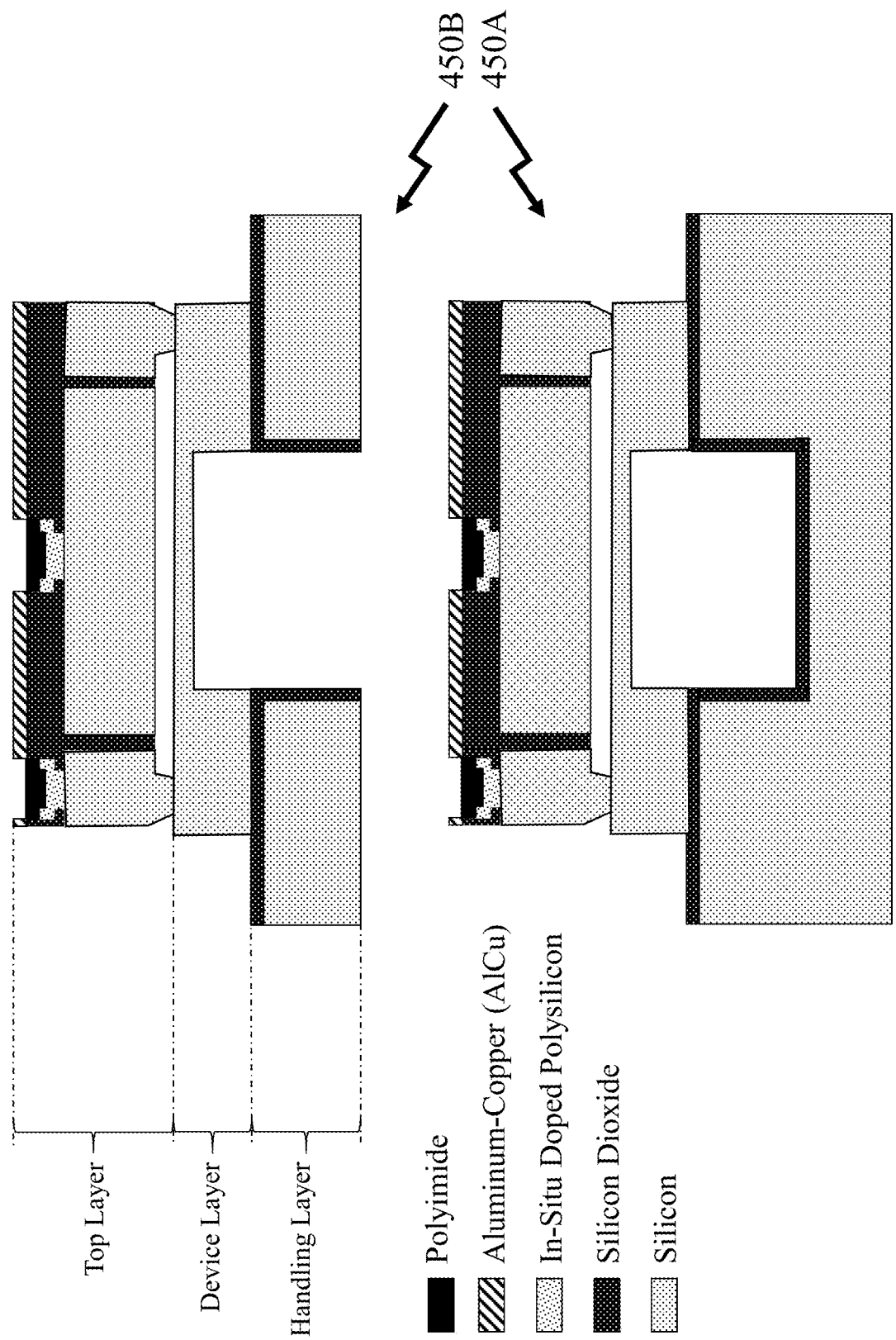
FIG. 4B depicts cross-sections of an absolute pressure sensor according to an embodiment of the invention as depicted in FIG. 4A before and after post-fabrication processing.
Figure 5A:
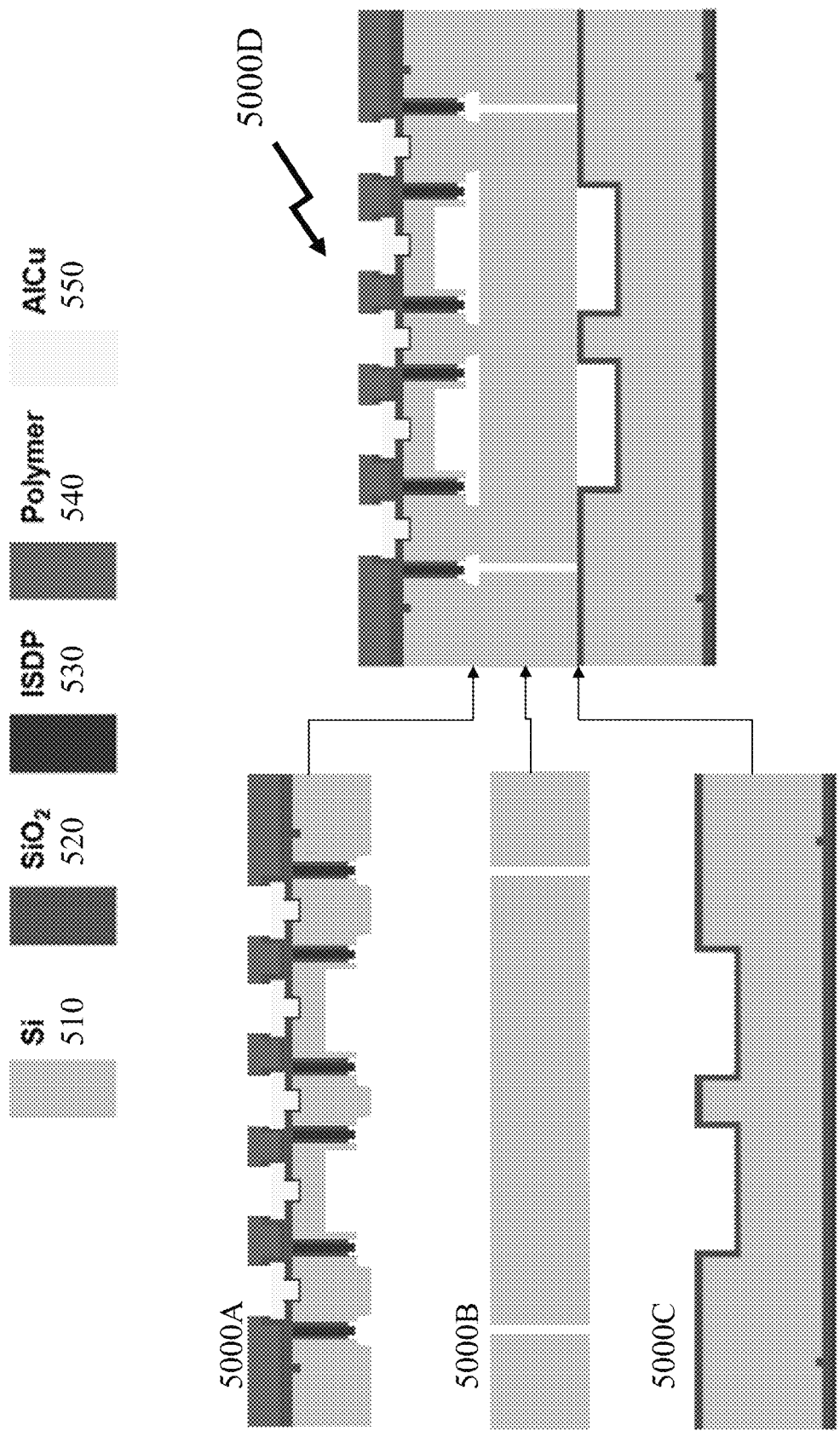
FIG. 5A depicts an exemplary MEMS pressure sensor fabrication methodology exploiting multiple silicon substrates.

Full details of the MEMS absolute pressure sensor may be found in U.S. Provisional Patent entitled "Microelectromechanical Devices and Systems" by V. Chodavarapu, A. Merdassi and G. Xereas. Amongst the main steps in the fabrication of the MEMS pressure sensor is the membrane patterning using the silicon structural layer, which may for example be 30 µm thick. The cavity is created using direct fusion bonding process of two silicon wafers by means of intermediate layer, e.g. 2 µm thickness. In order to fabricate the two electrodes without any short circuit, an insulating layer of oxide may be employed as depicted in first and second cross-sections 450A and 450B respectively in FIG. 4B for the MEMS pressure sensor before and after post-fabrication processing. Referring to FIG. 5A there is depicted an embodiment of the invention employing three silicon layers 5000A to 5000C wherein:

Top layer 5000A formed by micromachining a first silicon wafer such that it comprises the upper electrode, micromachined silicon to form the cavity and structures for fusion bonding the top layer to the device layer, wherein the top layer may be, for example, 90 µm thick;

Device layer 5000B which is etched in the post-processing to form the capacitive membrane and to which the top layer is fusion bonded, wherein the device layer may be, for example, 30 µm thick; and Handling layer 5000C which provides mechanical integrity and is etched to access the device layer during post-processing, wherein the handling layer may be, for example, 280 µm thick.

Figure 5B:
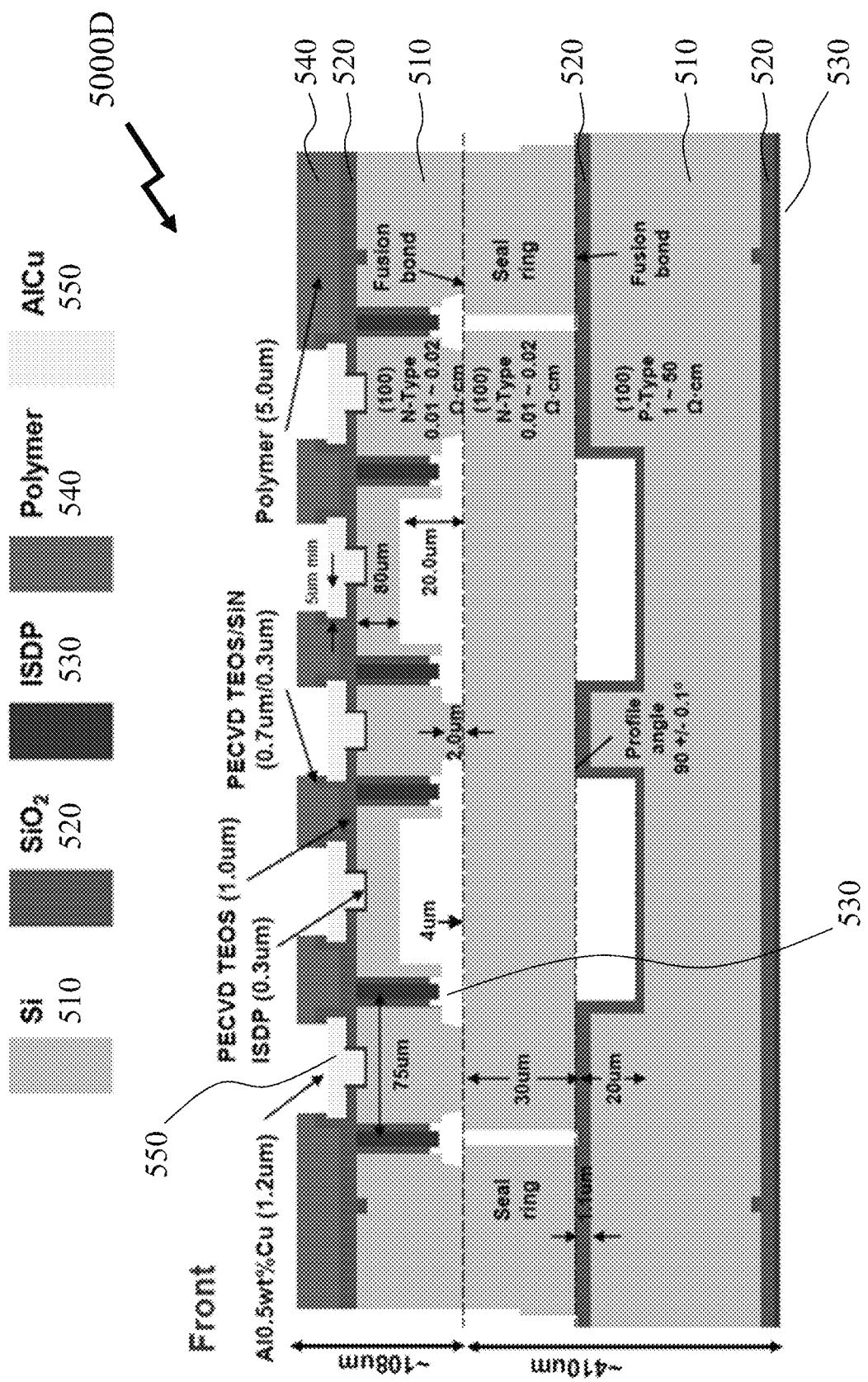
FIGS. 5B to 5F depict a post-processing sequence for providing MEMS pressure sensor membranes after initial wafer level encapsulation of pressure sensing cavities according to an embodiment of the invention.

These are bonded together to form wafer stack 5000D. As depicted the top layer 5000A is formed from silicon, in common with device layer 5000B and handling layer 5000C and has an upper surface of AlCu 550 metallisation contacting the silicon 510 through openings within a silicon dioxide ($SiO_2$) 520 layer with polymer 540 over-coating. Also disposed within the silicon are in-situ doped polysilicon (ISDP) 530 trench regions for mechanical integrity and isolation. Subsequently the wafer stack 5000D is post-processed in order to form the membranes of the pressure sensors within the handling wafer 5000C. This post-processing may exploit, for example, a four-step fabrication process once the top layer 5000A, device layer 5000B, and handling wafer 5000C have been processed and fusion bonded to each other to form the wafer stack 5000D. These four-steps being, for example, depicted in FIGS. 5C to 5F with respect to the wafer stack 5000D depicted in FIG. 5B which denotes thicknesses, materials, and geometries according to an embodiment of the invention supported by a commercial MEMS foundry.

Figure 5C:
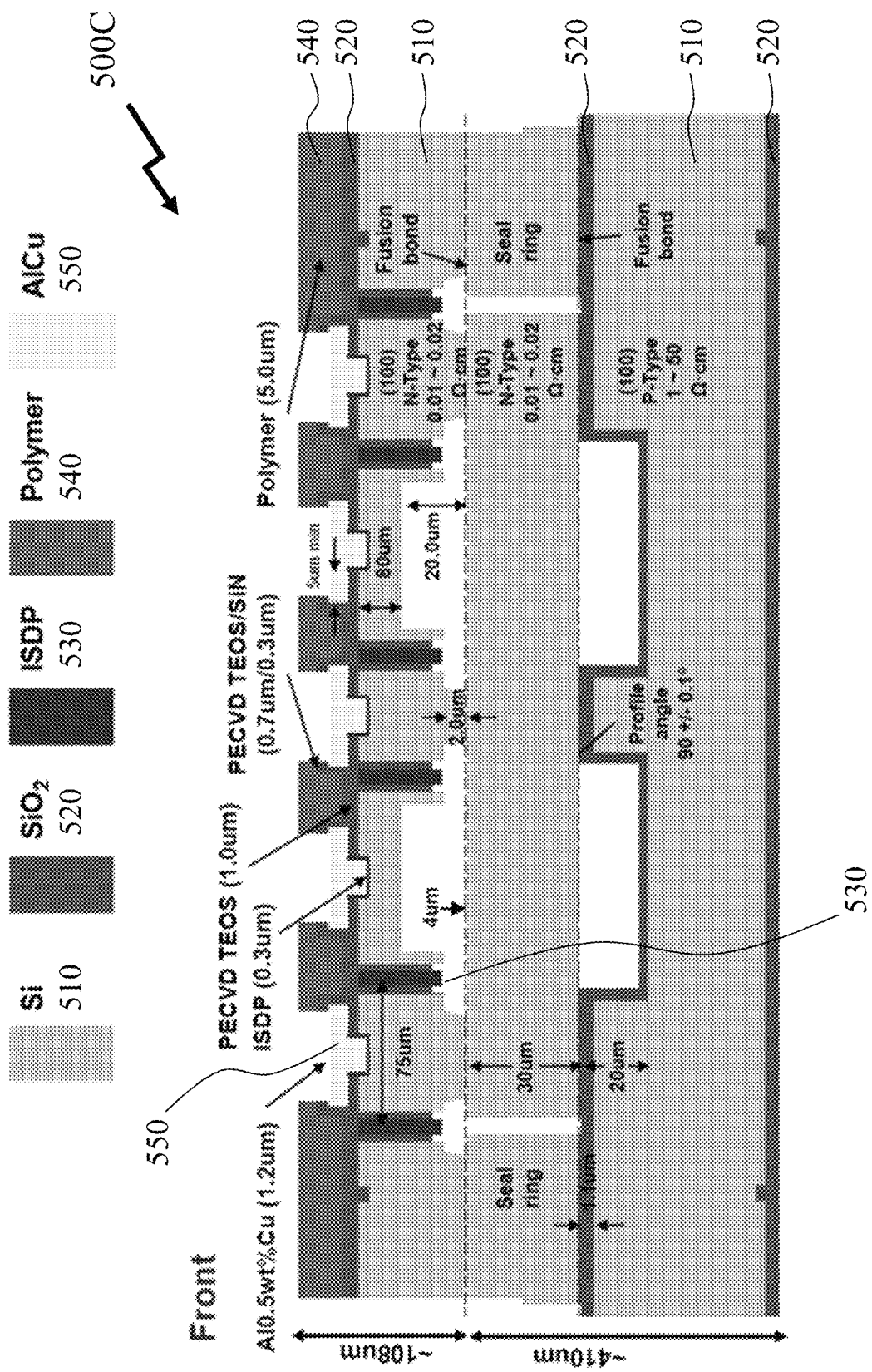
Figure 5D:
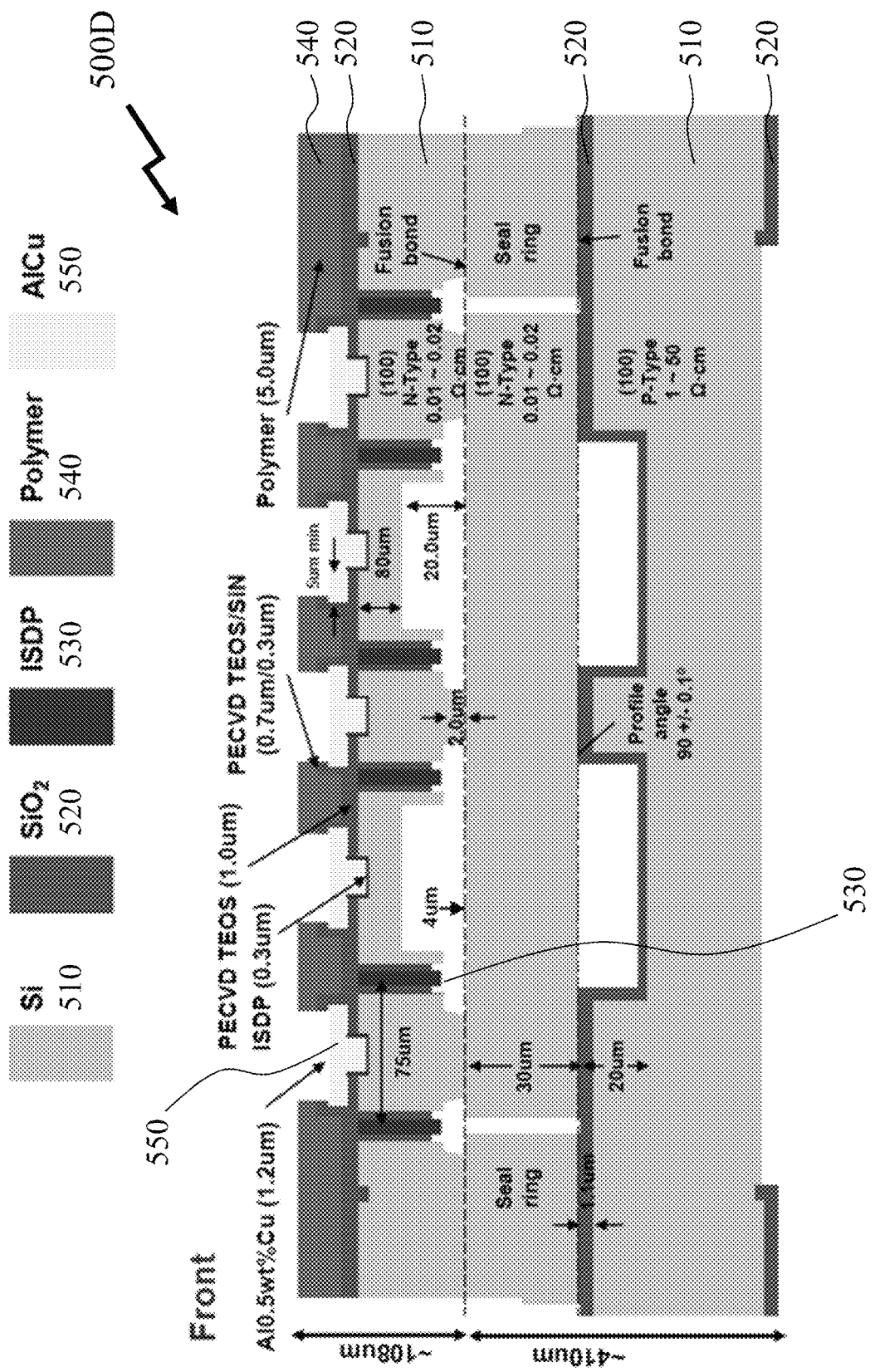
Figure 5E:
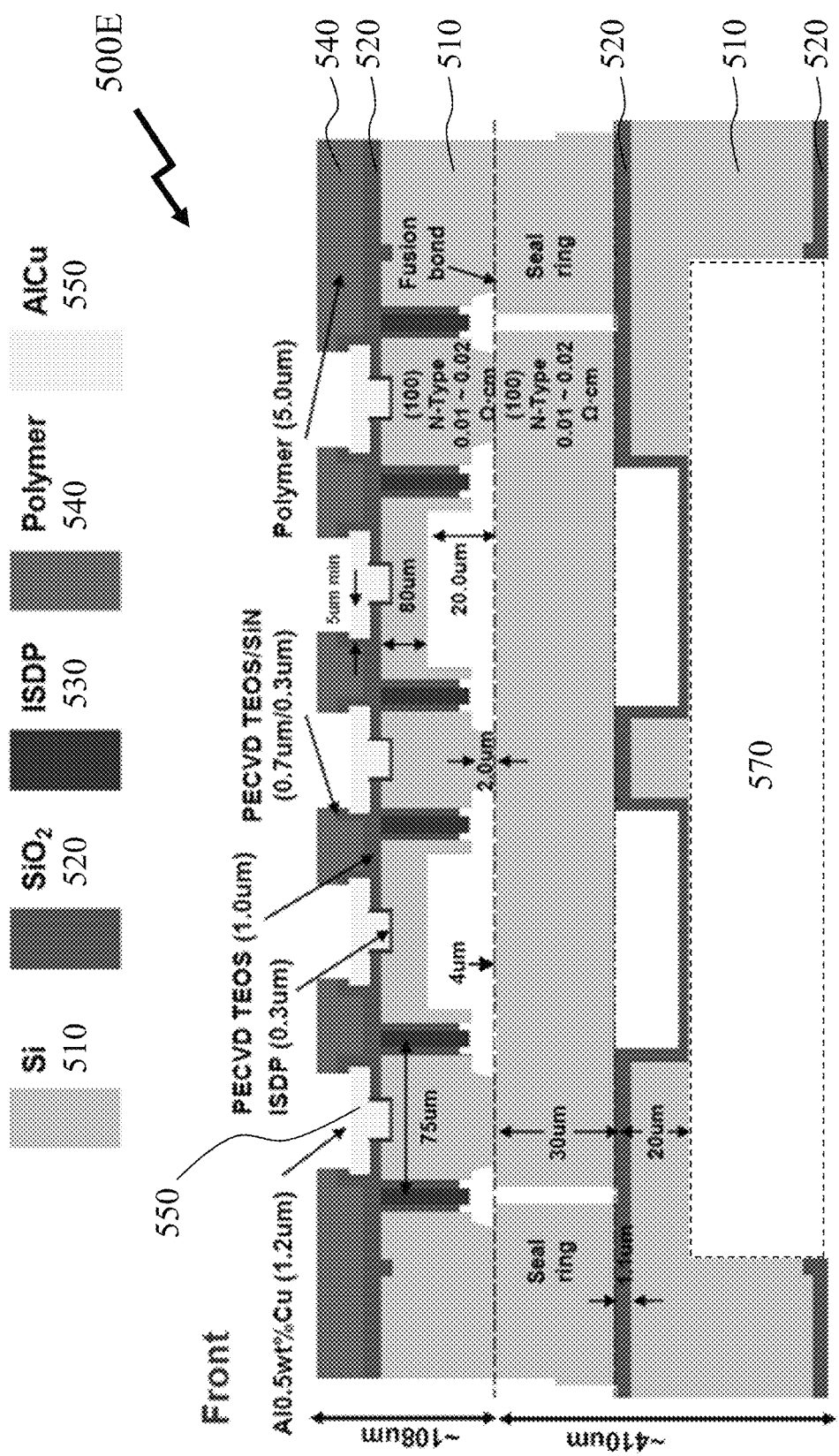
Figure 5F:
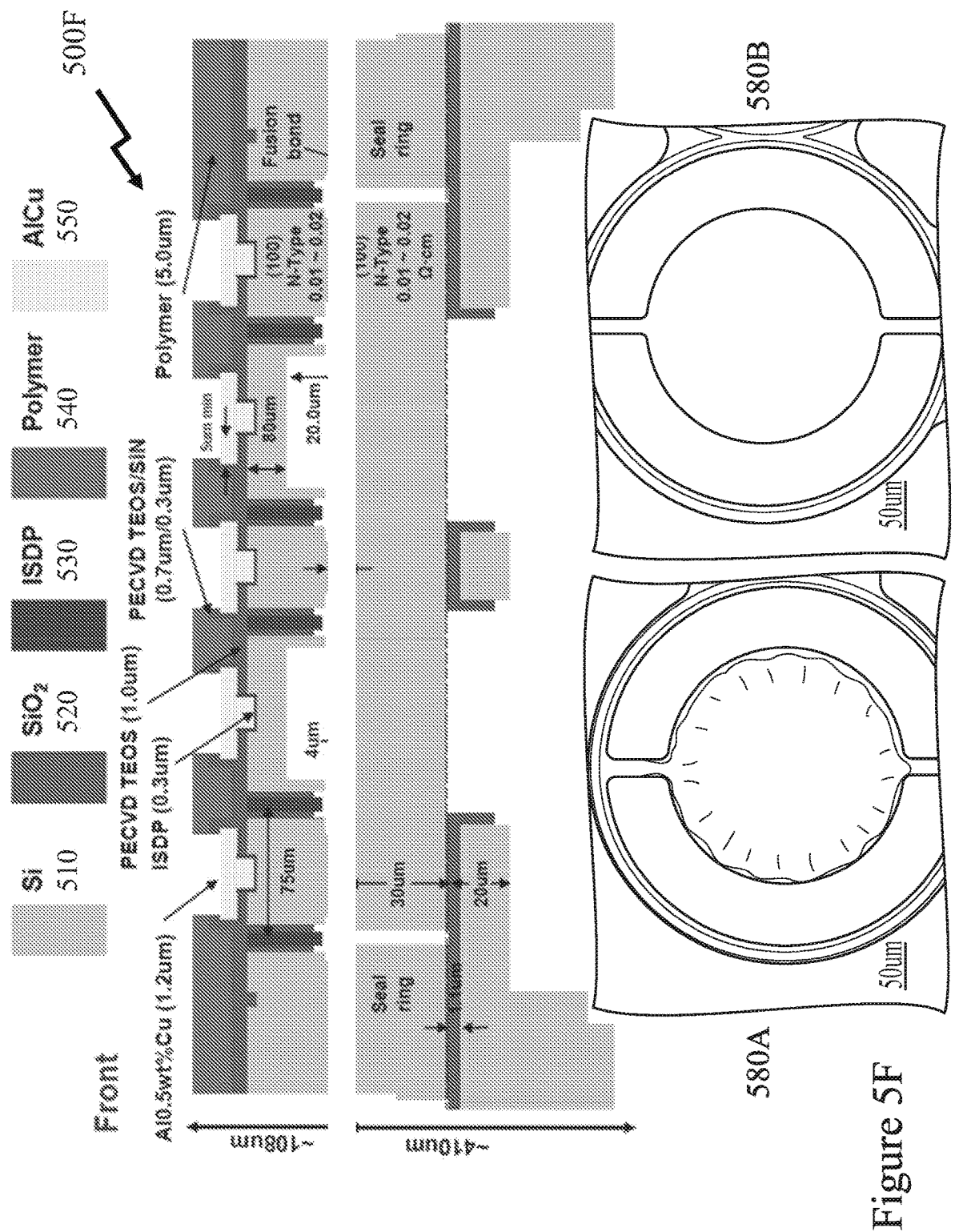
Figure 5G:
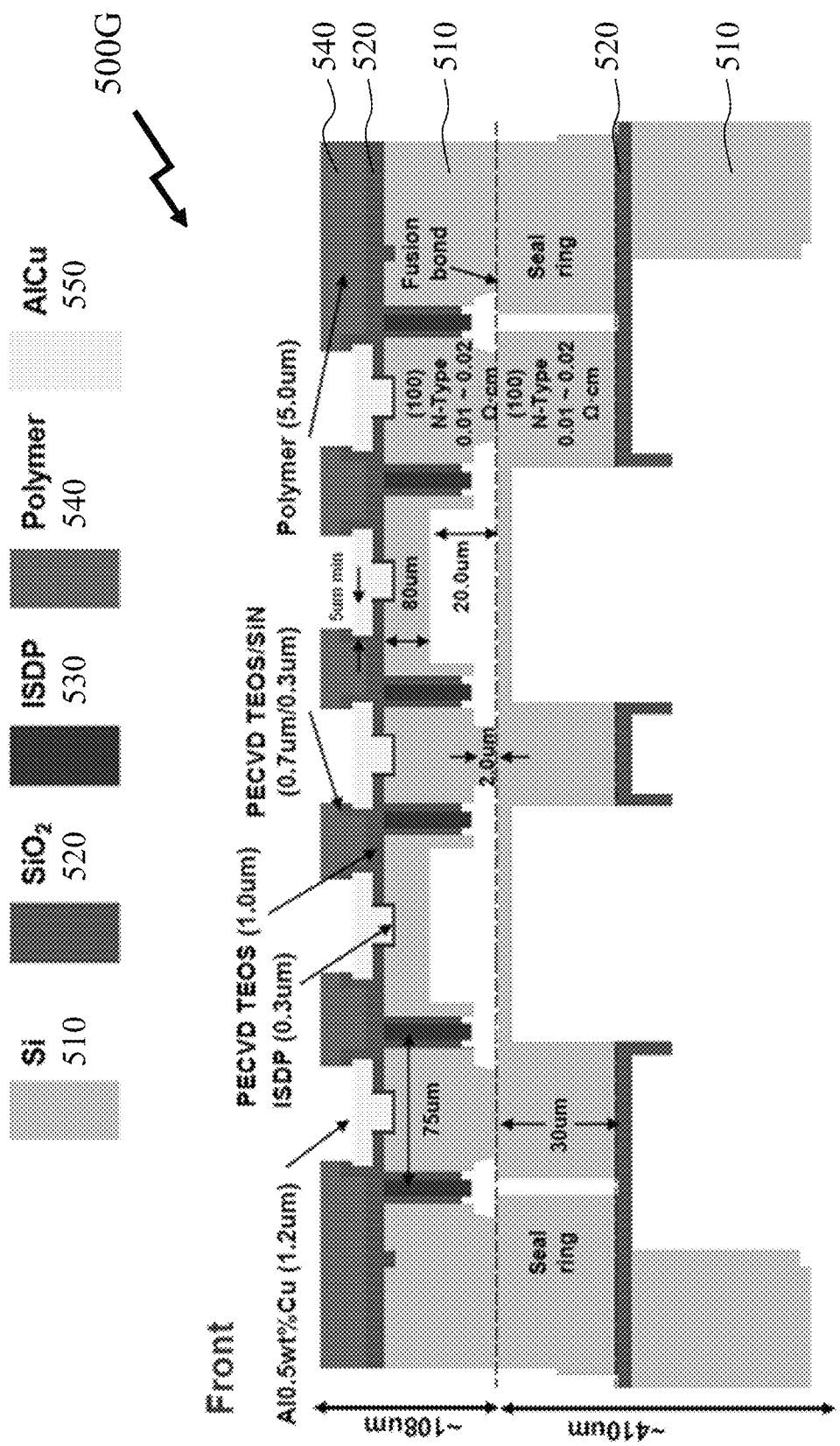
FIG. 5G depicts MEMS pressure sensor membranes according to an embodiment of the invention formed using an exemplary MEMS processing sequence.

Accordingly, these figures depict:

ISDP 530 etching in FIG. 5C yielding structure 500C wherein this ISDP is removed through a $SF_6$—$C_4F_8$ process within an RIE employing a 1500 W Inductively Coupled Plasma (ICP) source in conjunction with a 50 W RF excitation source;

Silicon dioxide 520 etching in FIG. 5D yielding structure 500D using an $CF_4$—He 2750 W ICP/100 W RF process wherein the backside $SiO_2$ is patterned and etched to expose the silicon 510 of the handling layer 5000C;

Silicon 510 etching in FIG. 5E yielding structure 500E using a multistep mask deposition and etching process to form the bottom cavity 570 wherein an etching process may, for example, comprise $SF_6$ (3 kW ICP/50 W RF) followed by $C_4F_8$ (3 kW ICP);

Silicon dioxide 520 etching in FIG. 5F yielding structure 500F using an $CF_4$—He 2750 W ICP/100 W RF process wherein the front surface $SiO_2$ on the handling layer 5000C exposed through the silicon 510 etching is removed leaving the openings formed within the original front surface of the handing wafer, wherein device layer 5000B/handling layer 5000C surfaces are depicted before and after this step in first and second images 580A and 580B respectively; and Device layer 5000B silicon 510 etching in FIG. 5G to yield finished structure 500G to form the membranes of the pressure sensors, wherein as with the silicon 510 etching in FIG. 5E a multistep mask deposition and etching process is employed comprising $SF_6$ (3 kW ICP/50 W RF) and $C_4F_8$ (3 kW ICP) etching removing, for example, approximately 0.5 µm per etch such that the number of etches, e.g. 40, 50, 56 yield membranes of 10 µm, 5 µm, and 2 µm from the initial 30 µm device layer 5000B thickness.

Figure 5H:
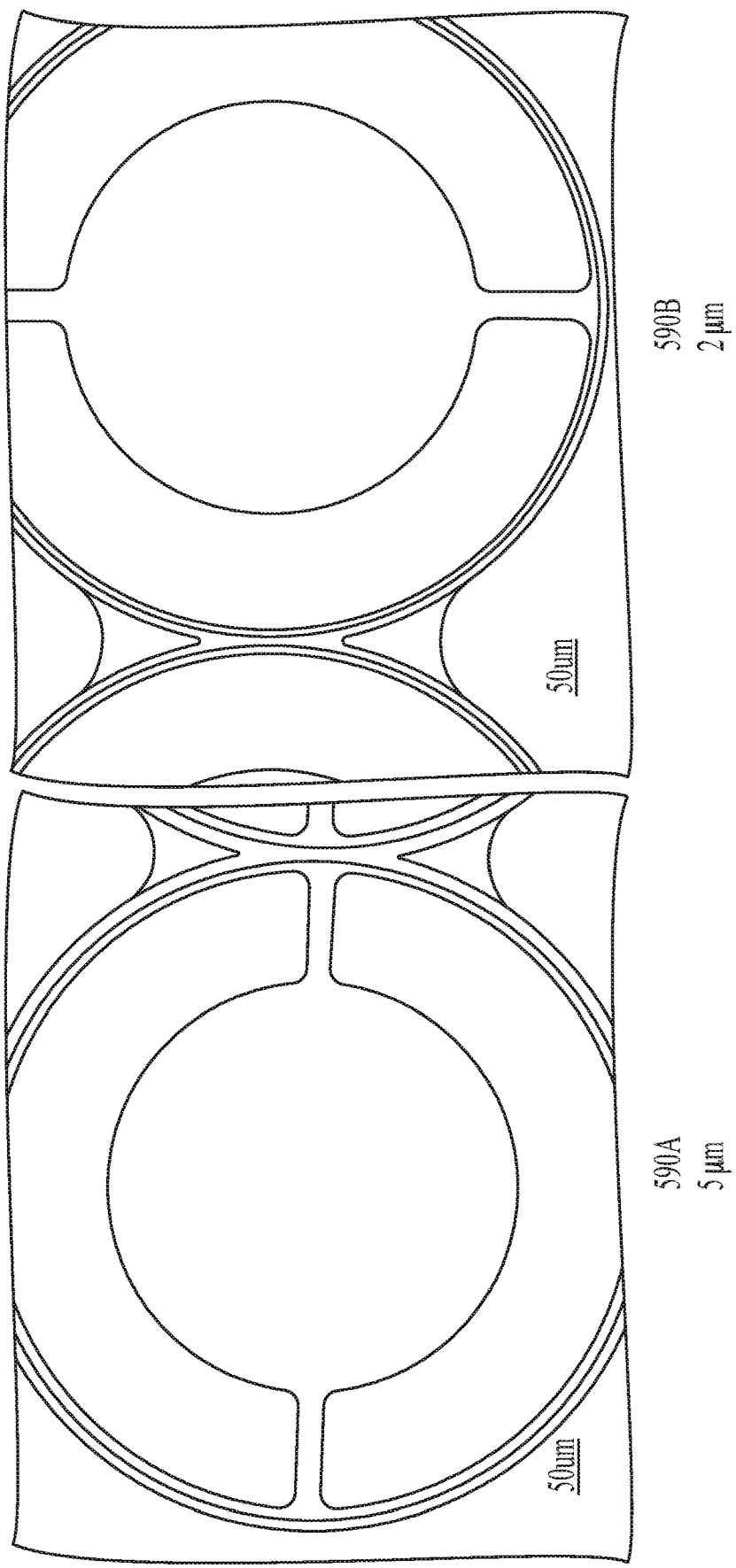
FIG. 5H depicts optical micrographs of fabricated MEMS pressure sensing membranes according to embodiments of the invention.
Figure 6:
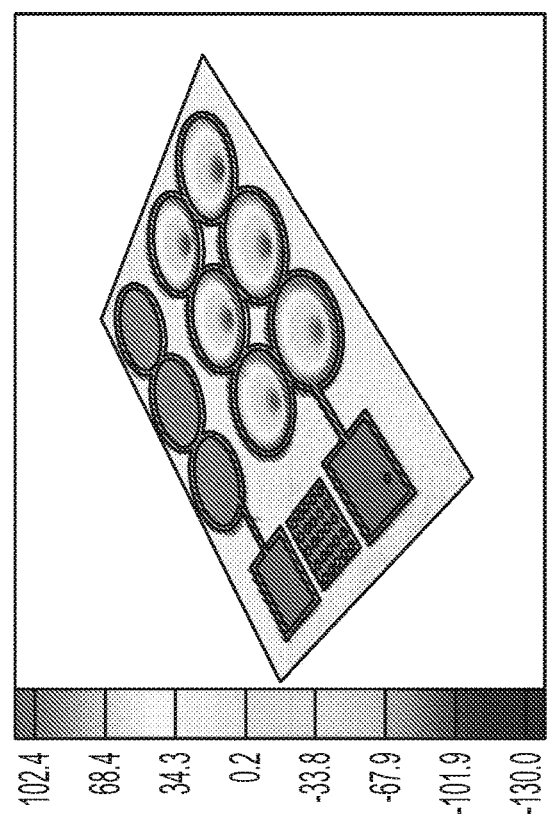
FIG. 6 depicts simulation of the deflection of the reference and sensing membranes for a MEMS pressure sensor according to an embodiment of the invention.

Referring to FIG. 5H there are depicted first and second optical micrographs 590A and 590B respectively of as fabricated 5 µm and 2 µm membranes respectively. Prototype pressure sensors consist of 6 sensing membranes and 3 reference membranes each of 200 µm diameter, as depicted in FIG. 3B with pressure sensor 300. This structure is also depicted in FIG. 6 with simulated deflection where the deflection of the 6 sensing membranes can be clearly seen together with the non-deflection of the reference elements. The output signal in response to ambient pressure is obtained by measuring the difference in the capacitance between the sensing and the reference membranes as shown in electrical model 350 in FIG. 3B.

Figure 7:
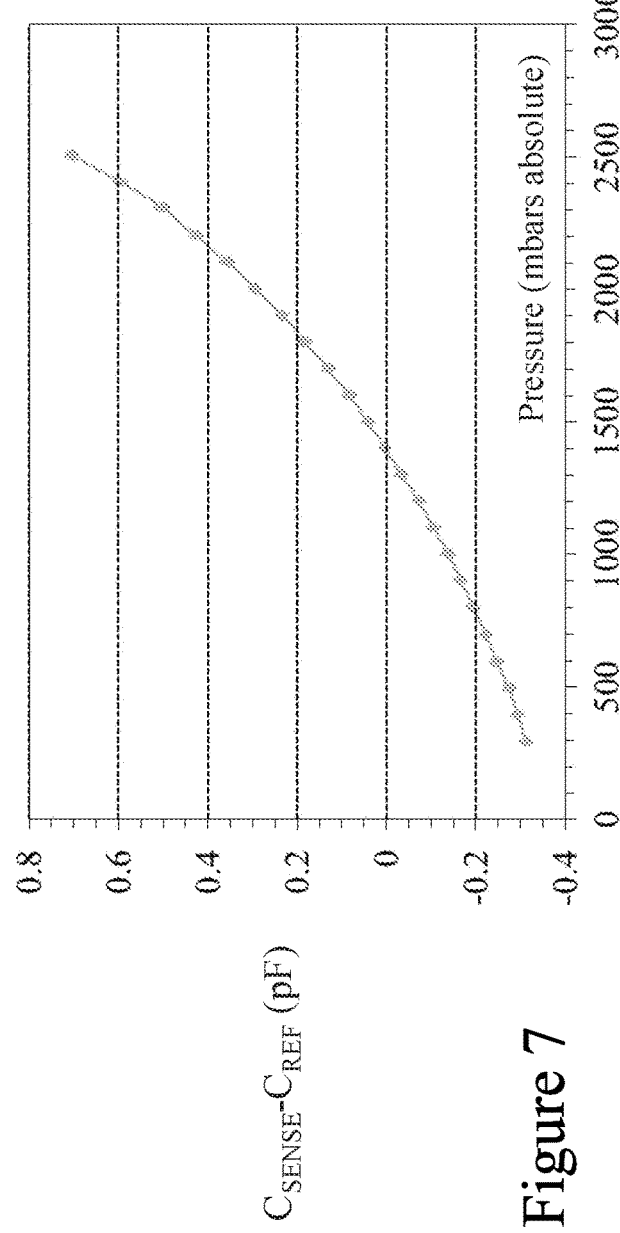
FIG. 7 depicts differential capacitance signals between the reference and sensing membranes in response to ambient pressures between 25 and 250 kPa for a MEMS pressure sensor according to an embodiment of the invention as depicted in FIG. 6.

Referring to FIG. 7 the difference between sensing capacitance, $C_{SENSE}$, and reference capacitance, $C_{REF}$. The pressure sensor is designed to operate most accurately from 25 kPa to 250 kPa as shown in FIG. 7. Current recommendations for intracompartmental pressure, see for example White et al in "Elevated Intramuscular Compartment Pressures Do Not Influence Outcome after Tibial Fracture" (J. Trauma, Vol. 55, pp. 1133-1138), set a threshold of 30 mmHg for intracompartmental pressure, whilst others suggest a difference of <30 mmHg between intracompartmental pressure and diastolic blood pressure, see for example McRae "Pocketbook of Orthopeaedics and Fractures". Generally, protocols set a typical tissue pressure range of 30-100 mmHg (~4 kPa-13.5 kPa) as that at which doctors perform fasciotomy to reduce compartment syndrome.

The pressure sensor will act as a stand-alone sensor as changes in compartment pressure is the most critical parameter to monitor. In addition to pressure, some literature has discussed temperature and partial pressure oxygen as an important differential diagnosis indicator. As noted supra the temperature sensor may be directly integrated into the RFIC 215 or alternatively it may be integrated into the capacitance to digital converter 220 or another silicon circuit within the implantable device. Oxygen partial pressure may be measured using optical techniques. Musallam et al in US Patent Publication US 2013/0,289,522 entitled "Methods and Systems for Closed Loop Neurotrophic Delivery Microsystems" discloses optically interrogated sensors and microchannel fluidics adaptable to integration upon silicon together with MEMS pressure sensor, for example.

The electrical model of the pressure sensor, depicted in electrical model 450 in FIG. 4, consists of two capacitors, $C_{SENSE}$ and $C_{REF}$, together with parasitic resistors, $R_{S1}, R_{S2}$, $R_{S3}, R_{P12}, R_{P23}$. Only $C_{SENSE}$ varies with the external applied pressure. $C_{REF}$ is constant regardless of the applied pressure, and is designed to be equal to $C_{SENSE}$ at a pressure of 1 atmosphere. Both $C_{SENSE}$ and $C_{REF}$ vary with temperature change. Two types of measurement methods can be used to measure the capacitance of the pressure sensor: (a) excitation can be applied on Pad 2, with differential measurement on Pad 1 and 3; or (b) two excitations in counter-phase can be applied on Pad 1 and 3, with measurement on Pad 2. In either method, the capacitance difference ($C_{SENSE}-C_{REF}$) is a function of the applied pressure. The pressure sensor can operate under pressure range $0 \leq P(mmHg) \leq 1875$ and temperature range $0 \leq T(°C.) \leq 125$ with typical a sensitivity of 0.4 fF/mmHg.

2.2 Capacitance Readout Asic Circuitry: A high resolution, low power, and 16-bit resolution capacitance readout ASIC circuitry may be used to directly transform the capacitance difference between $C_{SENSE}$ and $C_{REF}$ of the pressure sensor to a digital value. A microphotograph of an exemplary ASIC circuit for such a readout circuit is depicted in FIG. 3 having dimensions of approximately 3000 μm×1100 μm×450 μm (length×width×thickness). In this instantiation the ASIC circuit has the three pads of the pressure sensor connected to the capacitance readout ASIC circuitry wherein a Capacitance to Digital (C/D) converter directly converts the capacitance difference ($C_{SENSE}-C_{REF}$) into a digital output signal. There is an on-chip temperature sensor on the ASIC circuitry. The nonlinearity and temperature errors of the pressure sensor may be compensated, for example, with a multi-order polynomial compensation algorithm which is based on temperature measurement and correction parameters stored in the EEPROM memory block of the ASIC circuitry.

Using a wireless connection (an RF link at 13.56 MHz), the capacitance readout ASIC circuitry can be both powered and its output data transmitted. The ASIC circuitry is connected to a RF antenna, the power is harnessed through the antenna from a standard RFID reader and the internal signal clock is extracted from external RF signal. The ASIC circuitry stores identification information in the EEPROM memory, so that it can be inventoried and identified by the RF reader as with a conventional RFID tag. The ASIC circuitry is optimized for $600 \leq P(mmHg) \leq 1875$ pressure range and $20 \leq T(°C.) \leq 45$ temperature range with typical resolution of 0.75 mmHg and nonlinearity below 2%.

It would be evident that other readout circuit designs may be implemented without departing from the scope of the invention.

2.3 RF Reader and Antenna: Within an embodiment of the invention a commercial RFID reader may be employed to power the ASIC chip and read-out the pressure data wirelessly through an antenna, e.g. an SMA connectorised ferrite antenna. A commercial RFID reader allows for all of the Mandatory, Optional, Custom and Proprietary ISOIS693 commands for the 13.56 MHz transponder ICs. Modifications to a commercial reader may be required, for example within the application software, in order to adjust it to suit the capacitance readout ASIC circuitry. The software takes care of all communication between the ASIC circuitry, including: (1) send inventory command to identify if an ASIC circuitry/pressure sensor is available; (2) start temperature measurement and store the temperature value; (3) start pressure measurement and store the pressure value; (4) read, write and lock data inside the EEPROM of the ASIC circuitry. Alternatively, a custom RFID reader may be employed with bespoke software.

A typical pressure measurement sequence is as follows: first, the RF reader sends inventory command to check if there is an available ASIC circuitry/pressure sensor. If the sensor is powered up by the RF reader, it responds with its unit identification number and a check-sum. By this time, all the configuration and calibration data has been loaded from the non-volatile memory to the registers inside the ASIC circuitry. A temperature measurement is then performed at least one time before the pressure measurement. The calibration coefficients are calculated based on temperature data and on the coefficients stored within the EEPROM. A pressure measurement is then performed and the pressure value is calculated based on the calibration coefficients. These calibration coefficients are stored in registers and are used for each pressure measurement. They are updated following each temperature measurement. The temperature and pressure values are shown in hexadecimal format in the RFID reader software user interface.

It would be evident that other RF reader and antenna designs may be implemented without departing from the scope of the invention.

3. System Packaging 3.1 Prototype: The silicon MEMS pressure sensor and the ASIC circuitry within prototypes were glued on top of a Printed Circuit board (PCB) substrate using standard epoxy. The dimensions of the PCB substrate are 9 mm×2 mm×1.3 mm (length×width×thickness). Upon the PCB were copper pads and traces used to make connection between the ASIC circuitry and the external RF antenna. Aluminum wedge bonding, with 25 μm aluminum wire, was used to make connection between the MEMS sensor, ASIC circuitry and the PCB board.

Figure 8:
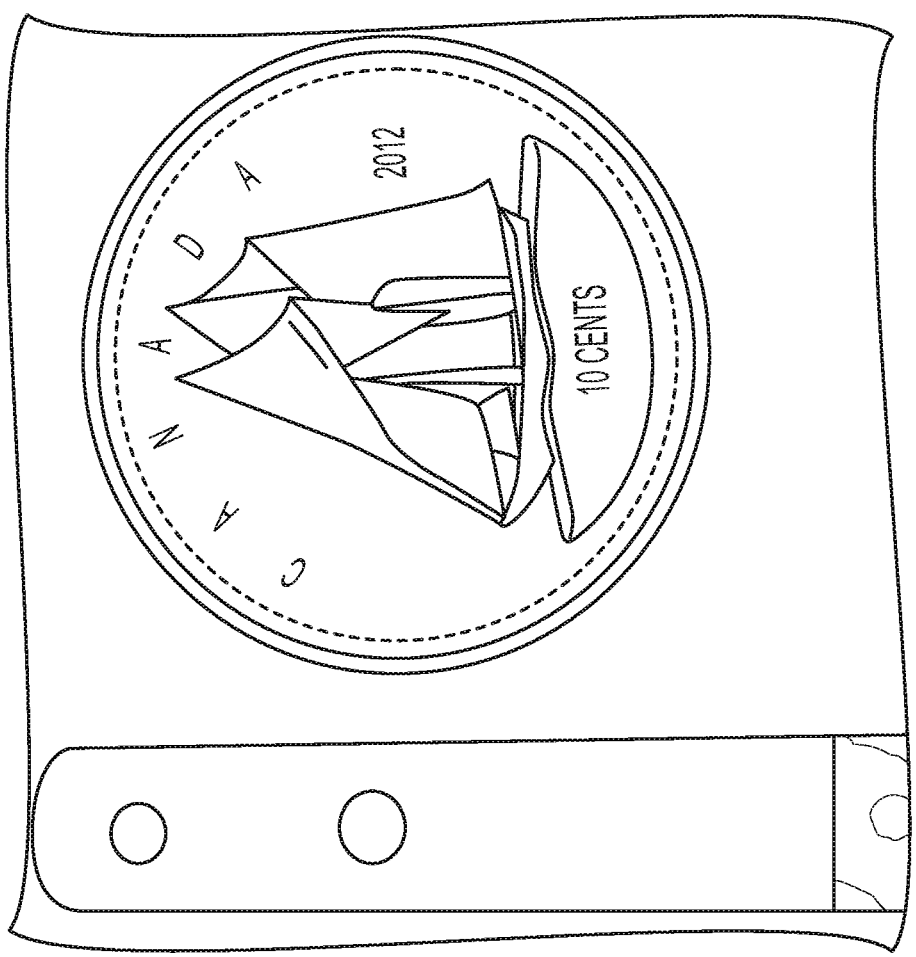
FIG. 8 depicts a prototype packaged implantable sensor with wireless read/power according to an embodiment of the invention.

The PCB with MEMS sensor and ASIC were packaged inside a hollow polytetrafluoroethylene (PTFE) tube implantable into limb compartments, as depicted in FIG. 7. PTFE is a biocompatible material, see for example Graffie in "Fluoropolymers: Fitting the Bill for Medical Applications" (Med. Dev. & Diag. Ind. Mag., October 2005, pp. 34-37), which will mitigate the body reactions induced by the implantation of the sensor system. The RF antenna is connected to the readout ASIC circuitry and was located in-vitro for initial prototype demonstrations. Wires were soldered to pads on the PCB board and their other ends connected to a SMA connectorised RF antennas. Potting of the assembly was undertaken within the prototypes using a two-part epoxy resin applied over the PCB board, the ASIC circuitry and the bonding pads of the pressure sensor. This resin forms a solid protection layer to protect the bonding wires and ASIC circuitry from damage during implantation and sensor use. Subsequently, a two-part silicone gel (MED-6640, Nusil Technology LLC) was applied over the PCB board, including the ASIC chip and the pressure sensor. The silicone gel cures in 30 minutes at ambient temperature and humidity. Application of the silicone gel is repeated for several times until the ASIC circuitry, pressure sensor and PCB board are completely covered by the silicone gel thereby making the overall sensor system biocompatible. The gel-coated PCB board with the ASIC chip and the MEMS pressure sensor were then inserted into the PTFE tube for syringe delivery. The assembled pressure sensor system after packaging is shown in FIG. 8 with a length and diameter of 22 mm and 4 mm, respectively.

Figure 9:
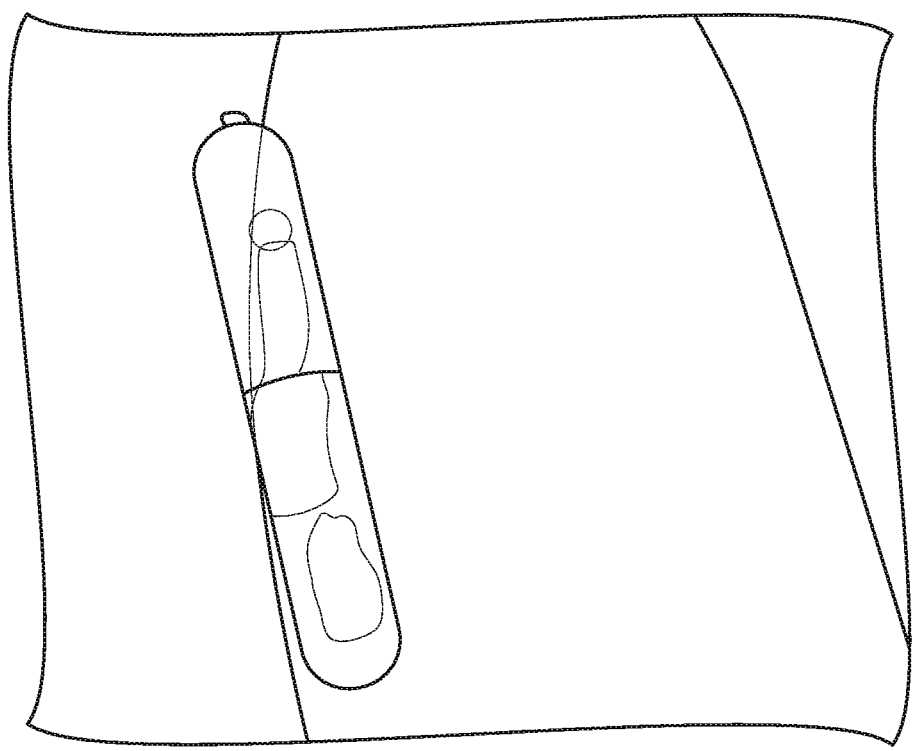
FIG. 9 depicts a prototype packaged implantable sensor with wireless read/power according to an embodiment of the invention.

It would be understood by one of skill in the art that biocompatible packaging of the sensor implant is an important challenge. Optionally, a biocompatible polymer layer such as Parylene-C may be employed although such polymers will typically significantly reduce the sensitivity of the pressure sensor as Parylene-C covers the capacitive membrane affecting their deflection. As a novel strategy to prevent biofouling and other potential problems the inventors exploit is a soft silicone cover. In one embodiment of the invention this is depicted as a discrete silicone cover to each of the MEMS pressure sensors in FIG. 2 which is then enclosed within a PEEK thermoplastic body which may be thinned or incorporate openings in those regions aligning with the MEMS pressure sensors. Such an assembled implantable RFID read pressure sensor is depicted in FIG. 9 with cylindrical shape 4 mm diameter and 23 mm in length where the clear thermoplastic body is visible with semi-opaque sleeve partially overlaid on the right hand side and without the thermoplastic tail for retrieval.

Figure 10:
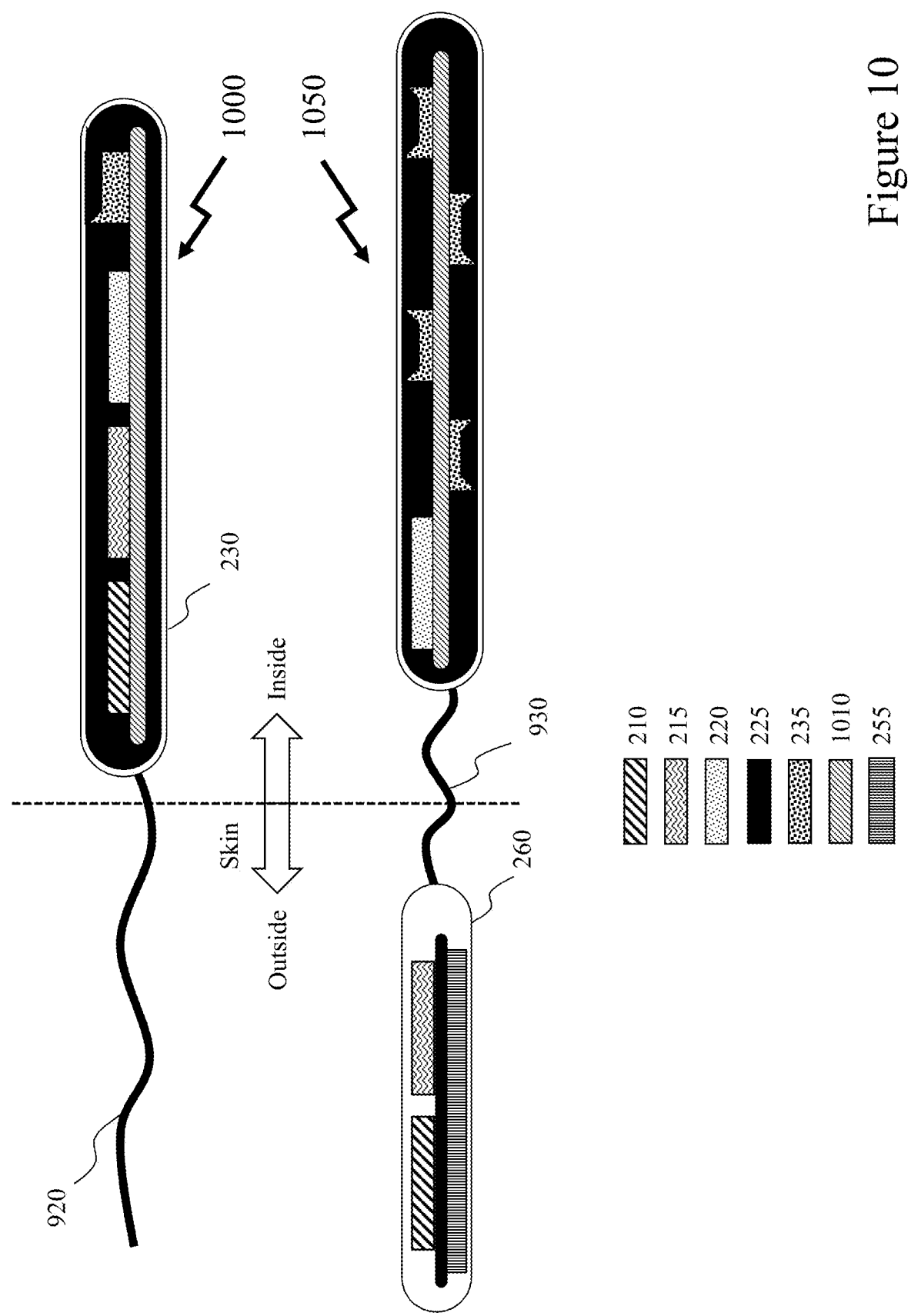
FIG. 10 depicts implantable sensors with implanted and external wireless read/power elements according to embodiments of the invention.

Within another embodiment of the invention as depicted in FIG. 10 with first and second embodiments 1000 and 1050 the implanted components are assembled onto a flexible substrate 1010 which is then cast into silicone either as a single process or through a use of a silicone cover (capsule) which is then filled inside with silicone paste. Such an approach would approximately translate the ambient pressures and temperature to the sensor system. This approach was selected because (i) silicone can be sterilized with standard procedures, (ii) the implant structure is compatible with performing the device implantation with a standard medical syringe, and (iii) the silicone cover approach is widely followed for cosmetic and plastic surgery implants. Implantation of sensor devices with a medical syringe is a standard approach of tagging animals, livestock, and humans that is approved by United States Food and Drug Association (US FDA).

The silicone implant will be glued to GORE-TEX® fabric as a tail that is few centimeters long. The tail 1020 as depicted in first embodiment 1000 in FIG. 10 is intended to remain partially protruding through the skin after implantation. This offers advantages for this application in that it can be used to pull out the device after the patient has recovered from critical traumatic conditions and when the need for monitoring has passed. This ensures that no sensors are missed and remain implanted in a patient for extended periods of time after the traumatic injury has occurred. Within second embodiment 1050 in FIG. 10 the tail provides management and protection of the power and data connections.

Thermoplastics such as polycarbonate and poly(aryl-ether-ether-ketone) (PEEK) are widely used in a variety of biomedical implants. In embodiments of the invention PEEK may be employed as it displays excellent material processing properties, mechanical strength, chemical inertness, and better biocompatibility, but is more expensive, as compared to polycarbonate. PEEK biomaterials are preferred in more demanding applications in trauma, orthopedic, and spinal implants. PEEK is now broadly accepted as a radiolucent alternative to metallic biomaterials. PEEK is suitable for the protective packaging of the electrical components and encapsulation of electrical wires. As a family of polymeric biomaterials, PEEK and its composites also provide implant designers with a broad range of mechanical behaviors from which to choose through the ability to engineer the fabrication of complex 3D microscale structures, plates, rods, fabrics, mesh, and larger biomechanical implants.

PEEK represents the dominant member of the polyaryletherketones (PAEK) polymers, and can be processed using a variety of commercial techniques, including injection molding, extrusion and compression molding, at temperatures between 390° C. and 420° C. At room and body temperature, PEEK is in its "glassy" state, as its glass transition temperature occurs about 143° C., whereas the crystalline melt transition temperature (Tm) occurs around 343° C. The important parameter here is its glass transition temperature which occurs at about 143° C. and which is lower than polycarbonate and within the normal range for packaging of electronics and MEMS components. Thermoplastic bonds also provide important hermetic sealing which helps ensure biocompatibility of the implantable devices.

In FIG. 2A where first and second embodiments 200 and 250 of the invention exploit a PEEK casing and tail then the body may be made with two halves with are prefabricated to include a cavity for placing the printed circuit board holding the RF antenna, RFID and MEMS pressure sensor. After placing the printed circuit board, the two halves are bonded together with heat. A PEEK fabric is used to prepare a sleeve pocket for holding the sensor body. The sleeve will be longer than the body. Using heat the sleeve will the bonded to the body and will extend outward as a tail.

Within applications of the invention multiple implanted sensors, e.g. 4, will provide coverage of all four compartments with a limb. Each sensor will typically be registered with an identification number which is transmitted in conjunction with the sensor data. In the second design, depicted in second embodiments 250 and 1050 in FIGS. 2 and 10 respectively hold multiple pressure sensors for distributed sensing application. Alternatively, the implantable section 2020 of the implantable sensor depicted in first image 2000A in FIG. 2B may exploit a multi-channel instrumentation amplifier 2050 coupled to multiple pressure sensors 2060 distributed along the encapsulated/coated section of the flexible polyimide circuit 2040.

Within embodiments of the invention the ACS sensor has been described as exploiting RFID/NFC technologies that operate typically at 13.56 MHz. However, other embodiments of the invention may exploit cellular wireless frequencies, e.g. 860-960 MHz, personal and/o body area networks, e.g. Bluetooth at 2.4 GHz. Alternatively, other frequencies and communications standards may be employed allowing collection of data over longer distances reaching several tens of meters. Within second embodiments 250 and 1050 in FIGS. 2 and 10 the wireless components including the RF antenna and RFIC are separately placed into another chamber, e.g. a second PEEK chamber, which is connected to the implanted ACS sensor body by the PEEK tail that encapsulates wires for the transfer of data between the two PEEK bodies. In the implantable sensor depicted in first image 2000A in FIG. 2B the wireless transmitter circuit 2030 is disposed externally and may be exposed such as where a packaged device is employed, encapsulated such as where a packaged device or flip-chip die are employed, or housed within a housing.

Optionally, the tail and second external chamber may be connected via a demountable connector allowing implanting and subsequent attachment of the second external chamber and/or replacement of the second external chamber.

Optionally, the capacitance to digital converter 220 may be disposed within the second external chamber rather than within the implanted chamber.

Optionally, the capacitance to digital converter 220 may be coupled to other sensor elements in addition to pressure sensors exploiting capacitance effects including, but not limited to, clamped beam resonators, tuning fork gyroscopes, and reference flow sensors.

Optionally, rather than exploiting an RFID/NFC reader a smartphone equipped with RFID/NFC interfaces may be employed. Optionally, the implanted sensor may communicate with the user's smartphone and/or other electrical devices (e.g. medical equipment) through an interface such as Bluetooth and the results processed and/or transferred to remote/local storage and/or applications via other wireless protocols, e.g. GSM, 4G, etc. as well as wired interfaces in instances of some medical equipment etc. Accordingly, a patient may be provided with an implanted sensor and the ongoing monitoring performed with or without periodic verification by a nurse or other medical personnel using an NFC/RFID reader. Potentially, the patient may even be released or always be an out-patient wherein monitoring is performed outside of a medical facility.

Figure 11:
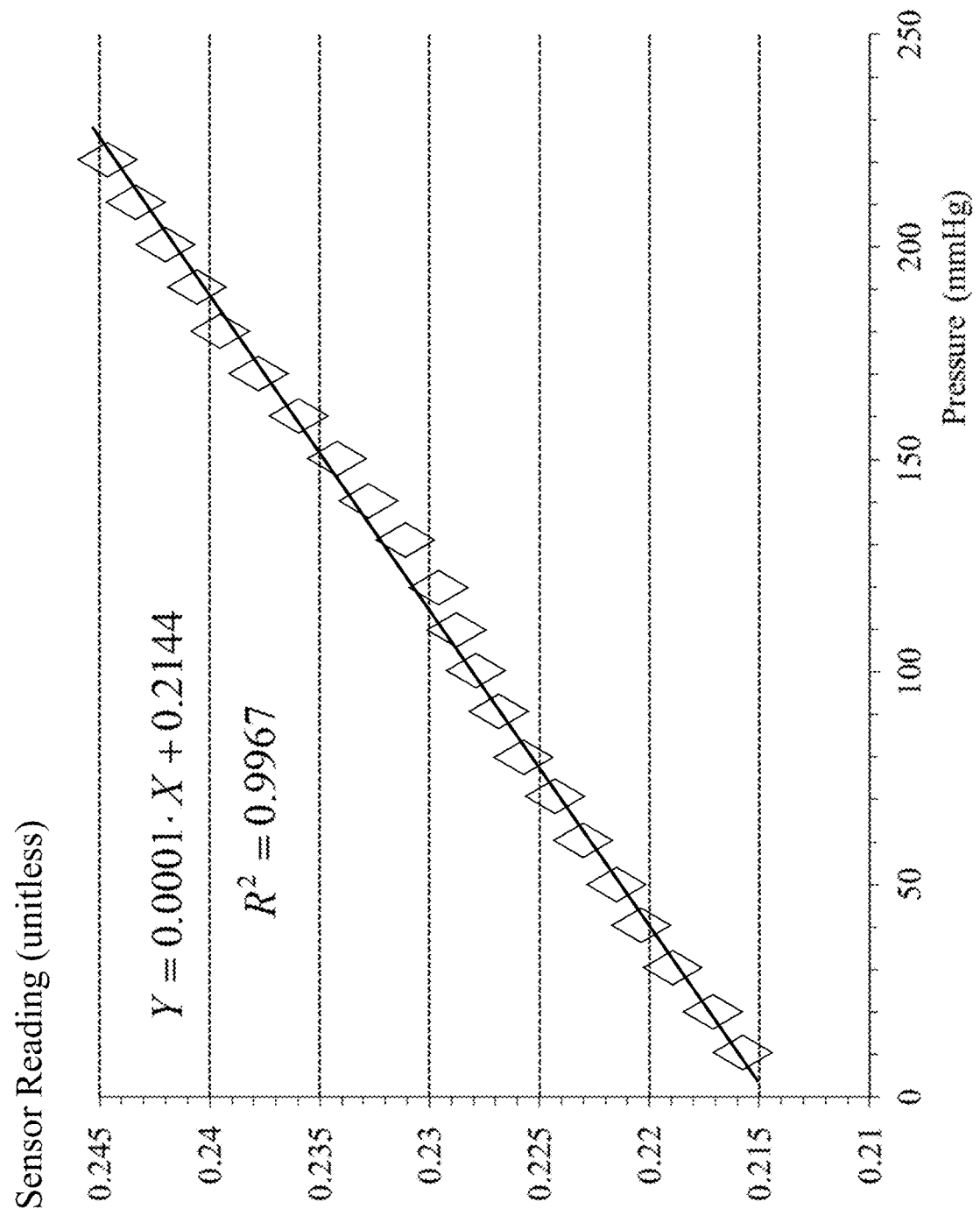
FIG. 11 depicts the sensor reading as a function of applied pressure for an implantable sensor according to an embodiment of the invention.
Figure 12:
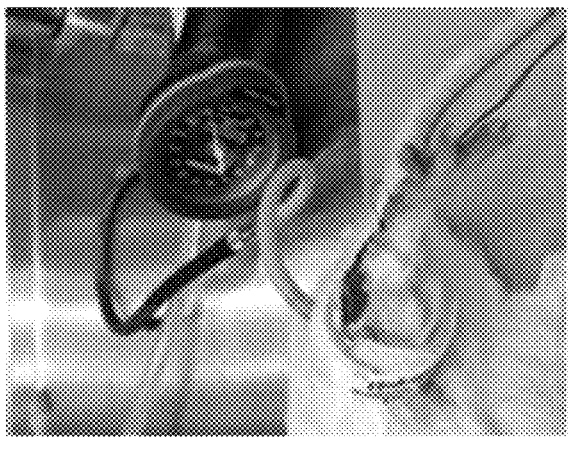
FIG. 12 depicts the testing of an implantable sensor according to an embodiment of the invention in rats.
Figure 12:
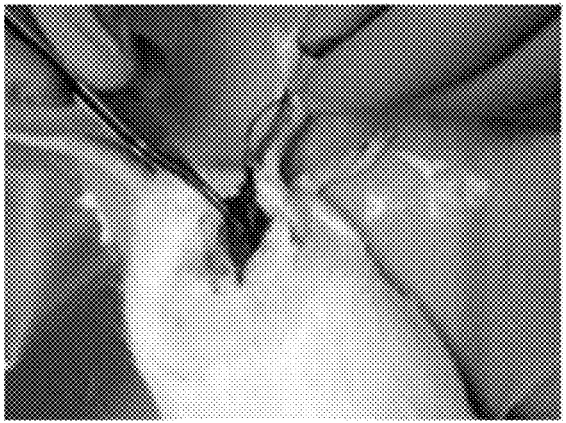
Figure 12:
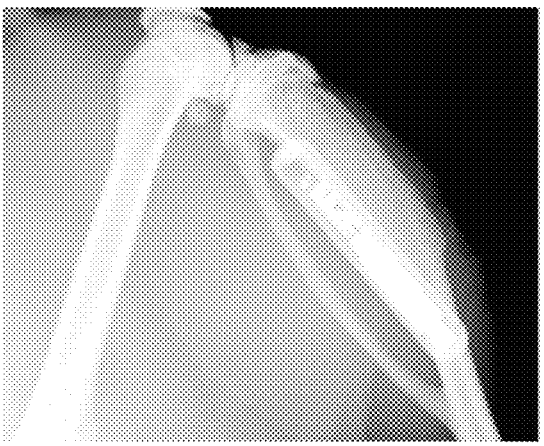

4. Experimental Results 4.1 Functional: A packaged pressure sensor system was placed into an airtight vessel together with a shock-proof blood pressure monitor which was used to pump air into the vessel to vary the pressure inside the vessel and as the pressure gauge to measure the actual pressure value. The vessel is immersed in a 37° C. water bath to mimic human body temperature. The sensor reading from the RF reader software interface for different pressures is recorded as shown in FIG. 11. As evident from FIG. 11, the reading shows good linearity between the sensor output and the applied pressure. The reading changes only 0.03 for pressure range of 220 mmHg as the embodiment of the invention employed had the sensing elements of the pressure sensor were covered by a thick silicone gel, which makes the pressure sensor less sensitive to the applied pressure. It would be evident that reducing the thickness of the silicone layer as described in embodiments of the invention will increase the responsiveness of the pressure sensor. In order to demonstrate the small dimensions of the implantable sensor and begin performing in-viva measurements the inventors have investigated the performance of the pressure sensor system by inducing ACS condition in the hind legs of a rat as depicted in FIG. 12 with first and second images 1200A and 1200B respectively. Third image 1250 depicts an X-ray image of an implanted sensor according to an embodiment of the invention implanted in a rat's tibia.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A pressure sensor device at least partially implantable into a body, comprising:
   a flexible circuit having a first surface and a second surface opposite the first surface, the flexible circuit being provided with at least one opening extending between the first surface and the second surface;
   an antenna for at least transmitting data;
   at least one pressure sensor mounted on the first surface of flexible circuit over a respective one of the at least one opening of the flexible circuit for measuring a pressure within the body, the measured pressure being coupled to the at least one pressure sensor through the respective one of the at least one opening of the flexible circuit;
   a wireless interface circuit connected to the antenna and the at least one pressure sensor, the wireless interface circuit for transmitting a signal indicative of the measured pressure via the antenna;
   an encapsulant deposited over at least a portion of the at least one pressure sensor and a portion of the flexible circuit including the first surface and excluding the second surface of the flexible circuit; and a flexible coating encapsulating at least the at least one pressure sensor and the encapsulant.

2. The pressure sensor device of claim 1, wherein the wireless interface circuit is adapted to convert an incoming wireless signal received by the antenna into electrical power for powering the pressure sensor device.

3. The pressure sensor device of claim 1, further comprising a battery for powering the pressure sensor device.

4. The pressure sensor device of claim 1, wherein the at least one pressure sensor comprises at least one pressure sensing element and at least one reference pressure element, and the measured pressure corresponds to an absolute pressure.

5. The pressure sensor device of claim 4, wherein the absolute pressure is determined based upon the capacitances of the at least one pressure sensing element and the at least one reference pressure element.

6. The pressure sensor device of claim 1, wherein the at least one opening is filled with the flexible coating.

7. The pressure sensor device of claim 1, wherein the encapsulant comprises a biocompatible material.

8. The pressure sensor device of claim 1, wherein the encapsulant is made of one of an epoxy and a thermoplastic adhesive.

9. The pressure sensor device of claim 1, wherein the at least one pressure sensor comprises at least one microelectromechanical systems (MEMS) pressure sensor.

10. The pressure sensor device of claim 1, wherein the flexible circuit is made of a polyimide material.

11. The pressure sensor device of claim 1, wherein the flexible coating is biocompatible and made of an elastomer material.

12. The pressure sensor device of claim 11, wherein the elastomer material comprises polyether ether ketone (PEEK).

13. The pressure sensor device of claim 1, wherein the antenna and the wireless interface circuit are mounted on the flexible circuit.

14. The pressure sensor device of claim 13, wherein the flexible coating further encapsulates the antenna and the wireless interface circuit.

15. The pressure sensor device of claim 1, comprising a first portion and a second portion, the flexible coating encapsulating only the first portion, the first portion comprising the at least one pressure sensor, the encapsulant and the flexible circuit and the second portion comprising the antenna and the wireless interface circuit.

16. The pressure sensor device of claim 15, further comprising a tail comprising electrical connections for connecting together the first and second portions.

17. The pressure sensor device of claim 1, further comprising a layer of silicone gel located between the at least one pressure sensor and the flexible coating.

18. The pressure sensor device of claim 1, wherein the antenna is operable over a predetermined wireless frequency range which is compatible with a wireless system operating according to a predetermined standard, the predetermined standard being at least one of radio frequency identification and near field communication.

19. The pressure sensor device of claim 1, wherein the wireless interface circuit is further adapted to transmit, along with the measured pressure, a unique identification code for the pressure sensor device stored within the wireless interface circuit.

20. The pressure sensor device of claim 1, wherein a thickness over the at least one pressure sensor is below a predetermined thickness to reduce a responsivity of the at least one pressure sensor by a predetermined amount relative to an unencapsulated pressure sensor.

\* \* \* \* \*